US010563267B2

(12) United States Patent
Lenz

(10) Patent No.: US 10,563,267 B2
(45) Date of Patent: Feb. 18, 2020

(54) POLYMORPHISM BIOMARKERS PREDICT CLINICAL OUTCOMES OF CANCER PATIENTS RECEIVING REGORAFENIB

(71) Applicant: Heinz-Josef Lenz, Los Angeles, CA (US)

(72) Inventor: Heinz-Josef Lenz, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/630,587

(22) Filed: Jun. 22, 2017

(65) Prior Publication Data

US 2017/0369949 A1    Dec. 28, 2017

Related U.S. Application Data

(60) Provisional application No. 62/353,487, filed on Jun. 22, 2016.

(51) Int. Cl.
*C12Q 1/68* (2018.01)
*C12Q 1/6886* (2018.01)
*A61K 31/4412* (2006.01)

(52) U.S. Cl.
CPC ........ *C12Q 1/6886* (2013.01); *A61K 31/4412* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

2013/0323734 A1* 12/2013 Kidd .................... C12Q 1/6886
435/6.11

OTHER PUBLICATIONS

Dorjgochoo, et al., "No association between genetic variants in angiogenesis and inflammation pathway genes and breast cancer survival among Chinese women", Cancer Epidemiology, 2013; 37:619-24.
Grothey, et al., "Regorafenib monotherapy for previously treated metastatic colorectal cancer (CORRECT): an international, multicentre, randomised, placebo-controlled, phase 3 trial", Lancet, 2013; 381:303-12.

Ishida, et al., "Pivotal role of the CCL5/CCR5 interaction for recruitment of endothelial progenitor cells in mouse wound healing", J Clin Invest, 2012; 122:711-21.
Kidd, et al., "Chemokine Ligand 5 (CCL5) and chemokine receptor (CCR5) genetic variants and prostate cancer risk among men of African Descent: a case-control study", Hered Cancer Clin Pract, 2012; 10:16.
Li, et al., "Regorafenib plus best supportive care versus placebo plus best supportive care in Asian patients with previously treated metastatic colorectal cancer (CONCUR): a randomised, double-blind, placebo-controlled, phase 3 trial", Lancet Oncol, 2015; 16:619-29.
Suenaga, et al., "Serum VEGF-A and CCL5 levels as candidate biomarkers for efficacy and toxicity of regorafenib in patients with metastatic colorectal cancer", Oncotarget, May 5, 2016. doi: 10.18632/oncotarget.9187.
Tabernero, et al., "Analysis of circulating DNA and protein biomarkers to predict the clinical activity of regorafenib and assess prognosis in patients with metastatic colorectal cancer: a retrospective, exploratory analysis of the CORRECT trial", Lancet Oncol., 2015; 16:937-48.
Wang, et la. "CCL5/CCR5 axis induces vascular endothelial growth factor mediated tumor angiogenesis in human osteosarcoma microenvironment", Carcinogenesis, 2015; 36:104-14.
Yoshino, et al., "Randomized phase III trial of regorafenib in metastatic colorectal cancer: analysis of the CORRECT Japanese and non-Japanese subpopulations", Invest New Drugs, 2015; 33:740-50.
Zhang, et al., "A novel role of hematopoietic CCL5 in promoting triple-negative mammary tumor progression by regulating generation of myeloid-derived suppressor cells", Cell Research, 2013; 23:394-408.

* cited by examiner

*Primary Examiner* — Jehanne S Sitton
(74) *Attorney, Agent, or Firm* — Foley & Lardner; Antoinette F. Konski; Peter Diez

(57) ABSTRACT

Methods are provided for determining whether a cancer patient is likely or not likely to experience HFSR (hand foot skin reaction) from a therapy comprising administration of an effective amount of regorafenib or an equivalent thereof, the methods including screening a biological sample isolated from the patient for the rs2280789 polymorphism, and/or the rs3817655 polymorphism. Methods are further provided for identifying the clinical outcome of cancer patients following a therapy comprising regorafenib or an equivalent thereof, the methods entailing screening a biological sample isolated from the patient for the rs7527092 polymorphism, and/or rs2071559 polymorphism. After determining if a patient is likely to be successfully treated, the disclosure also provides methods for treating the patient.

15 Claims, 9 Drawing Sheets
Specification includes a Sequence Listing.

FIG. 4

SEQUENCE LISTING

```
<160> NUMBER OF SEQ ID NOS: 27

<210> SEQ ID NO 1
<211> LENGTH: 51
<212> TYPE: DNA
<213> ORGANISM: Homo sapiens

<400> SEQUENCE: 1
atctcctgat cagtttttct gtcttyaagg tctacaccct caaggcctac a         51

<210> SEQ ID NO 2
<211> LENGTH: 51
<212> TYPE: DNA
<213> ORGANISM: Homo sapiens

<400> SEQUENCE: 2
gcttggagcc ctttgatcca acagawgagg aaatgttctc tccttaaaag c         51

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
atctccccaa catgagtcca                                              20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccatatgtcc tgttgtcctt ga                                           22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggcccagat tctaccacac                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctcatgggg aaggacagtt                                              20

<210> SEQ ID NO 7
<211> LENGTH: 51
<212> TYPE: DNA
<213> ORGANISM: Homo sapiens

<400> SEQUENCE: 7
tgagaccccg tctccattgt gtttaractt tcgtcttttt caaaaaaaaa a           51

<210> SEQ ID NO 8
<211> LENGTH: 51
<212> TYPE: DNA
<213> ORGANISM: Homo sapiens

<400> SEQUENCE: 8
aatattttgg gaaatagcgg gaatgytggc gaactgggca agtgcgtttt c           51

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aggatcaatt gaggccagga                                              20

<210> SEQ ID NO 10
<211> LENGTH: 27

-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgattaaata cattcctagt gttgtcc                                          27

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agggtatttt gtttggccag t                                                21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggctaggcag gtcacttcaa                                                  20

<210> SEQ ID NO 13
<211> LENGTH: 51
<212> TYPE: DNA
<213> ORGANISM: Homo sapiens

<400> SEQUENCE: 13
gatggacatc catagtcttt ctgtayctct aaaaattact actaatcttt g                51

<210> SEQ ID NO 14
<211> LENGTH: 51
<212> TYPE: DNA
<213> ORGANISM: Homo sapiens

<400> SEQUENCE: 14
tttaatagag caaggggagc ctgagygagt ccagcccacc atgttgctgg g                51

<210> SEQ ID NO 15
<211> LENGTH: 51
<212> TYPE: DNA
<213> ORGANISM: Homo sapiens

<400> SEQUENCE: 15
cggctaaggc tccccgagct gagccragtc tgacgtccct cactggcatg a                51

<210> SEQ ID NO 16
<211> LENGTH: 51
<212> TYPE: DNA
<213> ORGANISM: Homo sapiens

<400> SEQUENCE: 16
atgtcgacct cacaggtctg ccctghgggg caggaggagg ccggttggtc a                51

<210> SEQ ID NO 17
<211> LENGTH: 51

<212> TYPE: DNA
<213> ORGANISM: Homo sapiens

<400> SEQUENCE: 17
ctgggacctg ggcctatctt cttccytctc caggtacctt ctagtgggca g       51

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaggctgccc tgaggagt                                            18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgttgtgtgt catgccag                                            18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agaacgcact cgttgatgtc                                          20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtcacggaag cctactcctg                                          20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgtggtgatt tatggaaagg                                          20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic

```
            primer

<400> SEQUENCE: 23
gggagcatcc tgacaaaaga                                                    20

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcctttttat gtagctccac tgag                                               24

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aagcaaacat ctgaggcaca                                                    20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctggggtggt aggagcact                                                     19

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gagacggcca atgtcacc                                                      18
```

POLYMORPHISM BIOMARKERS PREDICT CLINICAL OUTCOMES OF CANCER PATIENTS RECEIVING REGORAFENIB

CROSS-REFERENCE TO RELATED APPLICATIONS

This application claims priority to U.S. provisional patent application No. 62/353,487, filed Jun. 22, 2016, the contents of which are incorporated herein by reference in its entirety

SEQUENCE LISTING

The instant application contains a Sequence Listing which has been submitted electronically in ASCII format and is hereby incorporated by reference in its entirety. Said ASCII copy, created on Aug. 3, 2017, is named 064189-9091 SL.txt and is 5,668 bytes in size.

BACKGROUND

In nature, organisms of the same species usually differ from each other in some aspects, e.g., their appearance. The differences are genetically determined and are referred to as polymorphism. Genetic polymorphism is the occurrence in a population of two or more genetically determined alternative phenotypes due to different alleles. Polymorphism can be observed at the level of the whole individual (phenotype), in variant forms of proteins and blood group substances (biochemical polymorphism), morphological features of chromosomes (chromosomal polymorphism) or at the level of DNA in differences of nucleotides (DNA polymorphism).

Polymorphism also plays a role in determining differences in an individual's response to drugs. Pharmacogenetics and pharmacogenomics are multidisciplinary research efforts to study the relationship between genotype, gene expression profiles, and phenotype, as expressed in variability between individuals in response to or toxicity from drugs. Indeed, it is now known that cancer chemotherapy is limited by the predisposition of specific populations to drug toxicity or poor drug response.

Although considerable research correlating gene expression and/or polymorphisms has been reported, much work remains to be done. This disclosure supplements the existing body of knowledge and provides related advantages as well.

Regorafenib (BAY 73-4506 and trade-named Stivarga®) is an oral multi-kinase inhibitor with known targeted activity against (VEGFR)-1,-2, and -3, FGFR-1, PDFR-α/Φ and ret, c-Kit, raf-1 kinases. It has been approved for treatment for metastatic colorectal cancer mCRC) and locally advanced gastrointestinal stromal cancer (GIST), with treatment for other types of tumors being explored.

SUMMARY

CCL5(RANTES)/VEGF-A pathway plays a critical role in development and progression of various cancers. As described herein, single nucleotide polymorphisms (SNPs) of CCL5 predict clinical outcomes in a therapy and severe hand foot skin reaction (HFSR) for cancer patients, the therapy comprising, or consisting essentially or, or yet further consisting of, regorafenib or an equivalent thereof. The genotype of G/G of the SNPs of CCL5 described herein predicts an ethnic difference in HFSR experienced by Caucasian (Italian) and Asian (Japanese) patients receiving a therapy comprising, or consisting essentially or, or yet further consisting of, regorafenib or an equivalent thereof. Furthermore, the genotype of G/G of the SNPs of CCL5 described herein predicts the CCL5 serum concentration through a therapy comprising, or consisting essentially or, or yet further consisting of, regorafenib or an equivalent thereof. The genotype of G/G of the SNPs of CCL5 described herein also predicts the VEGF-A serum concentration after a therapy comprising, or consisting essentially or, or yet further consisting of, regorafenib or an equivalent thereof.

It is described herein that cancer patients harboring certain genotypes are likely to experience more desirable clinical outcomes when treated with a therapy comprising, or consisting essentially of, or yet further consisting of, regorafenib or an equivalent thereof, as compared to those not having the genotype. More desirable clinical outcomes for a cancer patient following a therapy include, without limitation, higher likelihood to respond to the therapy, relatively longer progression free survival (PFS), relatively longer overall survival (OS), relatively longer time to tumor recurrence (TTR), lower likelihood to experience an adverse effect or toxicity, or relatively milder adverse effect or toxicity. One of the indication of toxicity is hand foot skin reaction (HFSR). In one aspect, the HFSR is Grade 1 or Grade 2, HFSR.

The findings of the present disclosure are summarized in the following two tables.

| Ethnicity | Polymorphism | Clinical Endpoint | Predicative Genotype |
|---|---|---|---|
| Asian | CCL5 rs2280789 | HFSR | G/G |
| Asian | CCL5 rs3817655 | HFSR | G/G |
| Caucasian | CCL5 rs2280789 | HFSR | G/G |
| Caucasian | CCL5 rs3817655 | HFSR | G/G |

| Polymorphism | Clinical Endpoint | Favorable Genotype for Regorafenib therapy | Unfavorable Genotype for Regorafenib therapy |
|---|---|---|---|
| TIE1 rs7527092 | OS | G/G or A/G | A/A |
| VEGFR2 rs2071559 | PFS, OS, Response | A/A or G/A | G/G |
| VEGFR2 rs2071559 and NOTCH1 rs6563 and ANG2 rs2442599 | PFS | G/G in VEGFR2 Any G in NOTCH1 Any G in ANG2 | G/G in VEGFR2 Any G in NOTCH1 A/A in ANG2 |
| TIE1 rs7527092 and Plgf rs2268614 | OS | A/A in TIE1 Any T in Plgf | A/A in TIE1 C/C in Plgf |
| VEGFR2 rs2071559 and NOTCH1 rs3125001 and ANG2 rs2916702 | Response | Any A in VEGFR2 C/C in NOTCH1 Any A in ANG2 | Any A in VEGFR2 C/C in NOTCH1 G/G in ANG2 |

** The genotypes noted here only refer to one DNA strand; for instance, genotype C/G is equivalent to G/C on the opposite strand and should be understood to encompass both strands. The rs2280789 polymorphism is located at chromosome position 35879999 on chromosome 17 according to the Genome Reference Consortium Human Build 38 patch release 2 (GRCh38.p2, NCBI). The rs2280789 polymorphism is located within the CCL family member 5 (CCL5). CCL5 is known as RANTES (regulated on activation, normal T cell expressed and secreted) and classified as a chemokine. CCL5 is chemotactic for T cells, eosinophils, and basophils, and actively localizes with leukocytes at inflammatory sites. CCL5 is identified as a late expression post T cell activation and interacts with CCR1, CCR3 and CCR5. The following nucleotide sequence represents a region of human DNA comprising the rs2280789 polymorphism:

(SEQ ID NO: 1)
ATCTCCTGATCAGTTTTTCTGTCTT[C/T]AAGGTCTACACCCTCAAGGC
CTACA.

The rs3817655 polymorphism is located at chromosome position 35872637 on chromosome 17 according to the Genome Reference Consortium Human Build 38 patch release 2 (GRCh38.p2, NCBI). The rs3817655 polymorphism is located within CCL5 gene as well. The following nucleotide sequence represents a region of human DNA comprising the rs3817655 polymorphism:

(SEQ ID NO: 2)
GCTTGGAGCCCTTTGATCCAACAGA[A/T]GAGGAAATGTTCTCTCCTTA
AAAGC.

The rs7527092 polymorphism is located at chromosome position 43301467 on chromosome 1 according to the Genome Reference Consortium Human Build 38 patch release 2 (GRCh38.p2, NCBI). The rs7527092 polymorphism is located within the TIE1 gene. TIE1 is an angiopoietin receptor, regulating cell adhesion molecules (CAMs) VCAM-1, E-selectin, and ICAM-1. Attachment of monocyte derived immune cells to endothelial cells is also enhanced by TIE1 expression. The following nucleotide sequence represents a region of human DNA comprising the rs7527092 polymorphism:

(SEQ ID NO: 7)
tgagacccgtaccaTTGTGTTTA[A/G]ACTTTCGTCTTTTTCAAAAAA
AAAA.

The rs2071559 polymorphism is located at chromosome position 55126199 on chromosome 4 according to the Genome Reference Consortium Human Build 38 patch release 2 (GRCh38.p2, NCBI). The rs2071559 polymorphism is located within the VEGFR2 gene. VEGFR2 is one of the three main subtypes of VEGFR (1,2, and 3), a signaling protein involved in both vasculogenesis and angiogenesis. The following nucleotide sequence represents a region of human DNA comprising the rs2071559 polymorphism:

(SEQ ID NO: 8)
AATATTTTGGGAAATAGCGGGAATG[C/T]TGGCGAACTGGGCAAGTGCG
TTTTC.

The rs2442599 polymorphism is located at chromosome position 6536630 on chromosome 8 according to the Genome Reference Consortium Human Build 38 patch release 2 (GRCh38.p2, NCBI). The rs2071559 polymorphism is located within the ANG2 gene. ANG2 is an antagonist of angiopoietin 1 (ANGPT1) and endothelial TEK tyrosine kinase (TIE-2, TEK), a protein that disrupts the vascular remodeling ability of ANGPT1 and may induce endothelial cell apoptosis. The following nucleotide sequence represents a region of human DNA comprising the rs2442599 polymorphism:

(SEQ ID NO: 13)
GATGGACATCCATAGTCTTTCTGTA[C/T]CTCTAAAAATTACTACTAAT
CTTTG.

The rs2916702 polymorphism is located at chromosome position 6503659 on chromosome 8 according to the Genome Reference Consortium Human Build 38 patch release 2 (GRCh38.p2, NCBI). The rs2916702 polymorphism is also located within the ANG2 gene. The following nucleotide sequence represents a region of human DNA comprising the rs2916702 polymorphism:

(SEQ ID NO: 14)
TTTAATAGAGCAAGGGGAGCCTGAG[C/T]GAGTCCAGCCCACCATGTTG
CTGGG.

The rs6563 polymorphism is located at chromosome position 136494732 on chromosome 9 according to the Genome Reference Consortium Human Build 38 patch release 2 (GRCh38.p2, NCBI). The rs6563 polymorphism is located within the NOTCH1 gene. NOTCH1 encodes Type I member of the NOTCH family of proteins, which share structural characteristics including an extracellular domain consisting of multiple epidermal growth factor-like (EGF) repeats, and an intracellular domain consisting of multiple different domain types. Notch signaling is an evolutionarily conserved intercellular signaling pathway that regulates interactions between physically adjacent cells through binding of Notch family receptors to their cognate ligands. The encoded preproprotein is proteolytically processed in the trans-Golgi network to generate two polypeptide chains that heterodimerize to form the mature cell-surface receptor. This receptor plays a role in the development of numerous cell and tissue types. Mutations in this gene are associated with aortic valve disease, Adams-Oliver syndrome, T-cell acute lymphoblastic leukemia, chronic lymphocytic leukemia, and head and neck squamous cell carcinoma. The following nucleotide sequence represents a region of human DNA comprising the rs6563 polymorphism:

(SEQ ID NO: 15)
CGGCTAAGGCTCCCCGAGCTGAGCC[A/G]AGTCTGACGTCCCTCACTGG
CATGA.

The rs3125001 polymorphism is located at chromosome position 136510809 on chromosome 9 according to the Genome Reference Consortium Human Build 38 patch release 2 (GRCh38.p2, NCBI). The rs3125001 polymorphism is also located within the NOTCH1 gene. The following nucleotide sequence represents a region of human DNA comprising the rs3125001 polymorphism:

(SEQ ID NO: 16)
ATGTCGACCTCACAGGTCTGCCCTG[A/C/T]GGGGCAGGAGGAGGCCG
GTTGGTCA.

The rs2268614 polymorphism is located at chromosome position 74949297 on chromosome 14 according to the Genome Reference Consortium Human Build 38 patch release 2 (GRCh38.p2, NCBI). The rs2268614 polymorphism is also located within the P(L)GF gene. PGF encodes a growth factor found in placenta which is homologous to vascular endothelial growth factor. Alternatively spliced transcripts encoding different isoforms have been found for this gene. The following nucleotide sequence represents a region of human DNA comprising the rs2268614 polymorphism:

(SEQ ID NO: 17)
CTGGGACCTGGGCCTATCTTCTTCC[C/T]TCTCCAGGTACCTTCTAGTG
GGCAG.

In some embodiments, provided are methods for determining whether a cancer patient is likely or not likely to experience HFSR (hand foot skin reaction) from a therapy comprising, or alternatively consisting essentially or, or yet further consisting of, an effective amount of regorafenib or an equivalent thereof, comprising screening a biological sample isolated from the patient for the rs2280789 polymorphism, and/or the rs3817655 polymorphism, wherein the presence of the genotype of (G/G) for the rs2280789, or (G/G) for rs3817655 indicates the patient will likely experience HFSR (hand foot skin reaction) and the absence of the (G/G) genotype indicates the patient is not likely to experience HFSR.

In some embodiments, screening a biological sample isolated from the patient for the rs2280789 polymorphism, and/or rs3817655 polymorphism comprises contacting the biological sample with a nucleic acid probe that specifically binds to nucleic acid containing the rs2280789, or rs3817655 polymorphism and overlaps the polymorphic site. For example, in some embodiments, the nucleic acid specifically binds to a nucleic acid having the sequence of any of SEQ ID NO: 1-2 and overlaps the polymorphic site. In some embodiments, the nucleic acid is labeled with a detectable moiety having about 5, about 10, about 15, about 20, about 25, about 30, about 35, or about 40 nucleotides upstream and/or downstream of the polymorphic region.

In some embodiments, screening a biological sample isolated from the patient for the rs2280789 polymorphism, and/or rs3817655 polymorphism comprises amplifying nucleic acid containing the rs2280789 polymorphism, and/ or rs3817655 polymorphism. In some embodiments, nucleic acid containing the rs2280789, and/or rs3817655 polymorphism is amplified using a forward primer and a reverse primer that flank each polymorphism. For example, nucleic acid containing the rs2280789 polymorphism is amplified using a forward primer comprising nucleic acid having the sequence of SEQ ID NO: 3 and a reverse primer comprising nucleic acid having the sequence of SEQ ID NO: 4, and/or nucleic acid containing the rs3817655 polymorphism is amplified using a forward primer comprising nucleic acid having the sequence of SEQ ID NO: 5 and a reverse primer comprising nucleic acid having the sequence of SEQ ID NO: 6.

In some aspect, the label is a fluorophore.

In some aspects, the patient suffers from colorectal cancer.

In some aspects, the patient suffers from gastrointestinal stromal cancer.

In some aspects, the patient suffers from non-metastatic cancer or metastatic cancer.

In some aspects, the biological sample is a tissue or a cell sample. In some aspects, the sample comprises at least one of a tumor cell, a normal cell adjacent to a tumor, a normal cell corresponding to the tumor tissue type, a blood cell, a peripheral blood lymphocyte, or combinations thereof.

In some aspects, the sample is at least one of blood, plasma, serum, an original sample recently isolated from the patient, a fixed tissue, a frozen tissue, a biopsy tissue, a resection tissue, a microdissected tissue, or combinations thereof.

In some aspects, the screening the rs2280789, and/or rs3817655 polymorphism is by a method comprising PCR, RT-PCR, real-time PCR, PCR-RFLP, sequencing, or nucleic probe hybridization in solution or on a solid support, such as a chip or a microarray. In some aspects, the patient is a human patient.

Also provided, in some embodiments, are kits for screening for determining whether a cancer patient is likely or not likely to experience HFSR from a therapy comprising, or consisting essentially of, or yet further consisting of, an effective amount of regorafenib or an equivalent thereof. In some embodiments, the kit comprises primer for amplification of nucleic acid containing the rs2280789, and/or rs3817655 polymorphism. In some embodiments, the kit comprises a nucleic acid probe that specifically binds to nucleic acid containing the rs2280789, and/or rs3817655 polymorphism and overlaps the polymorphic site. For example, in some embodiments, the nucleic acid probe specifically binds to a nucleic acid having the sequence of any of SEQ ID NO: 1-2 and overlaps the polymorphic site. In some embodiments, the nucleic acid probe has about 5, about 10, about 15, about 20, about 25, about 30, about 35 or about 40 or more contiguous nucleotides of any of SEQ ID NO: 1-2 and overlaps the polymorphic site.

In some embodiments, provided are methods for selecting a cancer patient for a therapy comprising, or consisting essentially of, or yet further consisting of, an effective amount of regorafenib or an equivalent thereof, comprising screening a biological sample isolated from the patient for the rs7527092 polymorphism, and/or rs2071559 polymorphism, and/or the combination of rs2071559 and rs6563 and rs2442599 polymorphism, and/or the combination of rs7527092 and rs2268614 polymorphism, and/or the combination of rs2071559 and rs3125001 and rs2916702 polymorphism, and selecting the patient for the therapy if the genotype of (A/G) or (G/G) for the rs7527092, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 is present in the sample. In some embodiments, the patient is not selected for a therapy comprising an effective amount of regorafenib or an equivalent thereof, if the genotype of (A/G) or (G/G) for the rs7527092, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 is not present in the sample. In some embodiments, the patient is not selected for a therapy comprising, or consisting essentially of, or yet further consisting of, an effective amount of regorafenib or an equivalent thereof, if the genotype of (A/A) for the rs7527092, or (G/G) for the rs2071559 or is present in the sample. In some embodiments, the patient is selected for a regorafenib-free and/or a regorafenib-equivalent-free therapy if the genotype (A/G) or (G/G) for the rs7527092, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 is not present in the sample. In some embodiments, the patient is selected for a regorafenib-free and/or a regorafenib-equivalent-free therapy if the genotype of (A/A) for the rs7527092, or (G/G) for the rs2071559, (G/G) for the rs2071559 and (A/A) for the rs6563 and (A/A) for the rs2442599, or (A/A) for the rs7527092 and (C/C) for the rs2268614, or (G/G) for the rs2071559 and (T/C) or (T/T) for the rs3125001 and (G/G) for the rs2916702 is present in the sample. In a further aspect, the therapy is a first line, second line, third line, fourth line or fifth line therapy. In a further aspect, the patient selected for the therapy is administered an effective amount of the regorafenib or an equivalent thereof.

Also provided, in some embodiments, are methods for classifying a cancer patient as eligible for a therapy comprising, or consisting essentially of, or yet further consisting of, regorafenib or an equivalent thereof, comprising screening a biological sample isolated from the patient for the rs7527092 polymorphism, and/or rs2071559 polymorphism, and/or the combination of rs2071559 and rs6563 and rs2442599, and/or the combination of rs7527092 and rs2268614, the combination of rs2071559 and rs3125001 and rs2916702, and classifying the patient as eligible for the therapy if the genotype of (A/G) or (G/G) for the rs7527092, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 is present in the sample. In some embodiments, the method comprises classifying the patient as not eligible for the therapy comprising, or consisting essentially of, or yet further consisting of, regorafenib or an equivalent thereof, if the genotype of (A/G) or (G/G) for the rs7527092, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 is not present in the sample. In some embodiments, the patient is classified as not eligible for the therapy comprising regorafenib or an equivalent thereof, if the genotype of (A/A) for the rs7527092, or (G/G) for the rs2071559, (G/G) for the rs2071559 and (A/A) for the rs6563 and (A/A) for the rs2442599, or (A/A) for the rs7527092 and (C/C) for the rs2268614, or (G/G) for the rs2071559 and (T/C) or (T/T) for the rs3125001 and (G/G) for the rs2916702 is present in the sample. In a further aspect, the therapy is a first line, second line, third line, fourth line or fifth line therapy. In some embodiments, the method further comprises administering a therapy comprising a therapeutically effective amount of regorafenib or an equivalent thereof.

Also provided, in some embodiments, are methods for identifying whether a cancer patient is likely to experience a relatively longer or shorter progression free survival (PFS) following a therapy comprising, or consisting essentially of, or yet further consisting of, an effective amount of regorafenib or an equivalent thereof, comprising screening a biological sample isolated from the patient for the rs2071559 polymorphism, and/or the combination of rs2071559 and rs6563 and rs2442599, and/or the combination of rs7527092 and rs2268614, and identifying that the patient is likely to experience a longer progression free survival if the genotype of (G/A) or (A/A) for the rs2071559, or (G/G) for the rs2071559 and (A/G) or (G/G) for the rs6563 and (A/G) or (G/G) for the rs2442599 is present in the sample, relative to a cancer patient not having the genotype. In some embodiments, the method comprises identifying that the patient is likely to experience a shorter progression free survival if the genotype of (G/A) or (A/A) for the rs2071559, or (G/G) for the rs2071559 and (A/G) or (G/G) for the rs6563 and (A/G) or (G/G) for the rs2442599 is not present in the sample, relative to a cancer patient not having the genotype or relative to a cancer patient having the genotype of (G/G) for the rs2071559. In some embodiments, the method comprises identifying that the patient is likely to experience a shorter progression free survival if the genotype of (G/G) for the rs2071559 or (G/G) for the rs2071559 and (A/A) for the rs6563 and (A/A) for the rs2442599 is present in the sample, relative to a cancer patient not having the genotype or relative to a cancer patient having the genotype of (G/A) or (A/A) for the rs2071559 or (G/G) for the rs2071559 and (A/A) for the rs6563 and (A/A) for the rs2442599.

Also provided, in some embodiments, are methods for increasing the progression-free and/or overall survival of a cancer patient, comprising screening a biological sample isolated from the patient for the rs7527092 polymorphism, and/or rs2071559 polymorphism, and/or the combination of rs2071559 and rs6563 and rs2442599, and/or the combination of rs7527092 and rs2268614, and classifying the patient as eligible for the therapy comprising an effective amount of regorafenib or an equivalent thereof, if the genotype of (A/G) or (G/G) for the rs7527092, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, is present in the sample, or not eligible for the therapy comprising, or consisting essentially of, or yet further consisting of, regorafenib or an equivalent thereof if the genotype of (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614 is not present in the sample. In some embodiments, the patient is classified as not eligible for the therapy comprising, or consisting essentially of, or yet further consisting of, an effective amount of regorafenib or an equivalent thereof, if the genotype of (A/A) for the rs7527092 or (G/G) for the rs2071559 is present in the sample. In some embodiments, the method further comprises administering a therapy comprising, or consisting essentially of, or yet further consisting of, an effective amount of regorafenib or an equivalent thereof, or a regorafenib-free or regorafenib-equivalent-free therapy in accordance with the classification.

Also provided, in some embodiments, are methods for increasing tumor response in a cancer patient, comprising screening a biological sample isolated from the patient for the rs2071559 polymorphism, and/or the combination of rs2071559 and rs3125001 and rs2916702, and classifying the patient as eligible for the therapy comprising an effective amount of regorafenib or an equivalent thereof, if the genotype of (G/A) or (A/A) for the rs2071559, or (A/G) or (A/A) for the rs2071559 and (C/C) for the rs3125001 and (A/G) or (A/A) for the rs2916702, is present in the sample, or not eligible for the therapy comprising, or consisting essentially of, or yet further consisting of, regorafenib or an equivalent thereof if the genotype of (G/A) or (A/A) for the rs2071559, or (A/G) or (A/A) for the rs2071559 and (C/C) for the rs3125001 and (A/G) or (A/A) for the rs2916702 is not present in the sample. In some embodiments, the patient is classified as not eligible for the therapy comprising, or consisting essentially of, or yet further consisting of, an effective amount of regorafenib or an equivalent thereof, if the genotype of (G/G) for the rs2071559 or (G/G) for the rs2071559 and (T/C) or (T/T) for the rs3125001 and (G/G) for the rs2916702 is present in the sample. In some embodiments, the method further comprises administering a therapy comprising, or consisting essentially of, or yet further consisting of, an effective amount of regorafenib or an equivalent thereof, or a regorafenib-free or regorafenib-equivalent-free therapy in accordance with the classification.

Also provided, in some embodiments, are methods for treating a cancer patient selected for treatment based on the presence of the genotype of (A/G) or (G/G) for the rs7527092 polymorphism, or (G/A) or (A/A) for the rs2071559 polymorphism in a biological sample from the patient, comprising administering to the patient a therapy comprising, or consisting essentially of, or yet further consisting of, an effective amount of regorafenib or an equivalent thereof. In some embodiments, the method further comprises screening a biological sample isolated from the patient for the rs7527092, and/or rs2071559 polymorphism. Thus, also provided, in some embodiments, are methods for treating a cancer patient, comprising screening a biological sample isolated from the patient for the rs7527092, and/or rs2071559 polymorphism and administering to the patient a therapy comprising, or consisting essentially of, or yet further consisting of, an effective amount of regorafenib or an equivalent thereof if the sample has the genotype of (A/G) or (G/G) for the rs7527092 polymorphism, or (G/A) or (A/A) for the rs2071559 polymorphism.

Also provided, in some embodiments, are methods for modifying the treatment of patient receiving a therapy comprising, or consisting essentially of, or yet further consisting of, an effective amount of regorafenib or an equivalent thereof based on the presence of the genotype of (A/G) or (G/G) for the rs7527092 polymorphism, or (G/A) or (A/A) for the rs2071559 polymorphism in a biological sample from the patient. For example, provided are methods for modifying the treatment of patient receiving a therapy comprising, or consisting essentially of, or yet further consisting of, an effective amount of regorafenib or an equivalent thereof, comprising screening a biological sample isolated from the patient for the rs7527092, and/or rs2071559 polymorphism, and modifying the dosage or frequency of the therapy comprising, or alternatively consisting essentially of, or yet further consists of, an effective amount of regorafenib or an equivalent thereof based on the genotype for rs7527092, and/or rs2071559. In some embodiments, the dosage or frequency of the therapy, or components thereof (e.g., one or more therapeutic agents of the therapy), is increased if the genotype of (A/G) or (G/G) for the rs7527092, or (G/A) or (A/A) for the rs2071559 is not present in the sample. In some embodiments, the dosage or frequency of the therapy, or components thereof, is increased if the genotype of (A/A) for the rs7527092, or (G/G) for the rs2071559 is present in the sample. In some embodiments, the therapy is discontinued if the genotype of (G/G) for rs1792689, (C/T) or (C/C) for rs2268753, or (G/G) for rs17776182 is not present in the sample. In some embodiments, the therapy is discontinued if the genotype of (A/A) for the rs7527092, or (G/G) for the rs2071559 is present in the sample. In some embodiments, the therapy is continued if the genotype of (A/G) or (G/G) for the rs7527092, or (G/A) or (A/A) for the rs2071559 is present in the sample.

In some embodiments, screening a biological sample isolated from the patient for the rs7527092 polymorphism, and/or rs2071559 polymorphism comprises contacting the biological sample with a nucleic acid probe that specifically binds to nucleic acid containing the rs7527092, and/or rs2071559 polymorphism and overlaps the polymorphic site. For example, in some embodiments, the nucleic acid specifically binds to a nucleic acid having the sequence of any of SEQ ID NO: 7-8 and overlaps the polymorphic site. In some embodiments, the nucleic acid is labeled with a detectable moiety having about 5, about 10, about 15, about 20, about 25, about 30, about 35, or about 40 nucleotides upstream and/or downstream of the polymorphic region.

In some embodiments, screening a biological sample isolated from the patient for the rs7527092 polymorphism, and/or rs2071559 polymorphism comprises amplifying nucleic acid containing the rs7527092, and/or rs2071559 polymorphism. In some embodiments, nucleic acid containing the rs7527092, and/or rs2071559 polymorphism is amplified using a forward primer and a reverse primer that flank each polymorphism. For example, nucleic acid containing the rs7527092 polymorphism is amplified using a forward primer comprising nucleic acid having the sequence of SEQ ID NO: 9 and a reverse primer comprising nucleic acid having the sequence of SEQ ID NO: 10, and/or nucleic acid containing the rs2071559 polymorphism is amplified using a forward primer comprising nucleic acid having the sequence of SEQ ID NO: 11 and a reverse primer comprising nucleic acid having the sequence of SEQ ID NO: 12.

In some embodiments, screening a biological sample isolated from the patient for the combination of rs2071559 and rs6563 and rs2442599 polymorphism, and/or the combination of rs7527092 and rs2268614 polymorphism, and/or the combination of rs2071559 and rs3125001 and rs2916702 polymorphism comprises contacting the biological sample with nucleic acids from a group of nucleic acids one by one, without ordering, the group of nucleic acids including a nucleic acid probe that specifically binds to nucleic acid containing the rs7527092, a nucleic acid probe that specifically binds to nucleic acid containing the rs6563, a nucleic acid probe that specifically binds to nucleic acid containing the rs2071559; a nucleic acid probe that specifically binds to nucleic acid containing the rs7527092, a nucleic acid probe that specifically binds to nucleic acid containing the rs2268614, a nucleic acid probe that specifically binds to nucleic acid containing the rs2071559, a nucleic acid probe that specifically binds to nucleic acid containing the rs3125001. The contacting of the biological sample with the group of nucleic acids can be done in any order. In some aspect, the label is a fluorophore.

In some aspects, the patient suffers from colorectal cancer.

In some aspects, the patient suffers from gastrointestinal stromal cancer.

In some aspects, the patient suffers from non-metastatic cancer or metastatic cancer.

In some aspects, the biological sample is a tissue or a cell sample. In some aspects, the sample comprises at least one of a tumor cell, a normal cell adjacent to a tumor, a normal cell corresponding to the tumor tissue type, a blood cell, serum, a peripheral blood lymphocyte, or combinations thereof.

In some aspects, the sample is at least one of blood, plasma, serum, an original sample recently isolated from the patient, a fixed tissue, a frozen tissue, a biopsy tissue, a resection tissue, a microdissected tissue, or combinations thereof.

In some aspects, the screening the rs7527092, and/or rs2071559, and/or the combination of rs2071559 and rs6563 and rs2442599 and/or the combination of rs7527092 and rs2268614, and/or the combination of rs2071559 and rs3125001 and rs2916702 polymorphism is by a method comprising PCR, RT-PCR, real-time PCR, PCR-RFLP, sequencing, or nucleic probe hybridization in solution or on a solid support, such as a chip or a microarray. In some aspects, the patient is a human patient.

Also provided, in some embodiments, are kits for screening for selecting a cancer patient for a therapy comprising an effective amount of regorafenib or an equivalent thereof, or for classifying a cancer patient as eligible for a therapy comprising an effective amount of regorafenib or an equivalent thereof, or for identifying whether a cancer patient is likely to experience a relatively longer or shorter progression free survival following a therapy comprising an effective amount of regorafenib or an equivalent thereof. In some embodiments, the kit comprises primer for amplification of nucleic acid containing the rs7527092, and/or rs2071559, and/or rs6563, and/or rs2268614, and/or rs2071559, and/or rs312500, and/or rs2916702 polymorphism. In some embodiments, the kit comprises a nucleic acid probe that specifically binds to nucleic acid containing the rs7527092, and/or rs2071559, and/or any individual polymorphism of the combination of rs2071559 and rs6563 and rs2442599 and/or any individual polymorphism of the combination of rs7527092 and rs2268614, and/or any individual polymorphism of the combination of rs2071559 and rs3125001 and rs2916702 polymorphism and overlaps the polymorphic site. For example, in some embodiments, the nucleic acid probe specifically binds to a nucleic acid having the sequence of any of SEQ ID NO: 7-8, 13-17 and overlaps the polymorphic site. In some embodiments, the nucleic acid probe has about 5, about 10, about 15, about 20, about 25, about 30, about 35 or about 40 or more contiguous nucleotides of any of SEQ ID NO: 7-8, 13-17 and overlaps the polymorphic site.

BRIEF DESCRIPTION OF THE DRAWINGS

Figure 4:
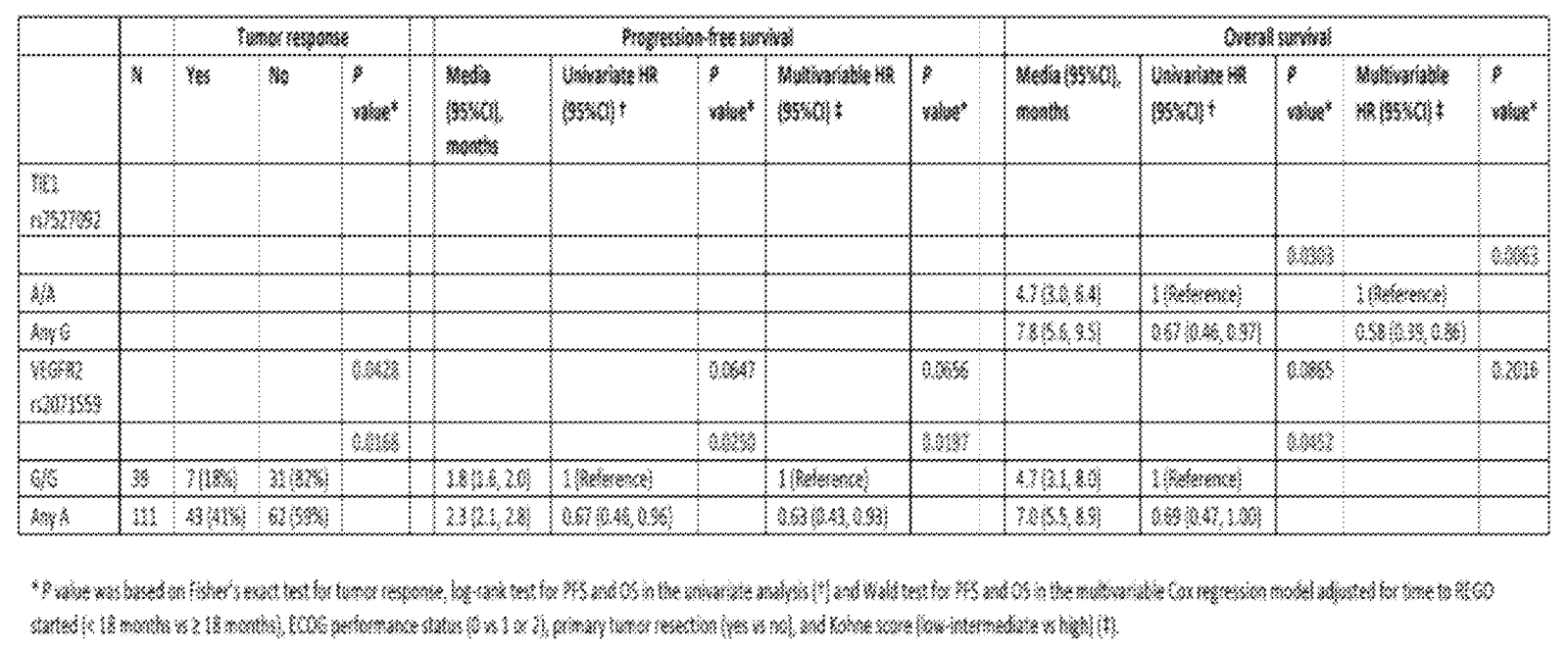

FIG. 4 illustrates data for correlation of various SNPs with the clinical outcomes on patients receiving regorafenib treatment.

DETAILED DESCRIPTION

Figure 1:
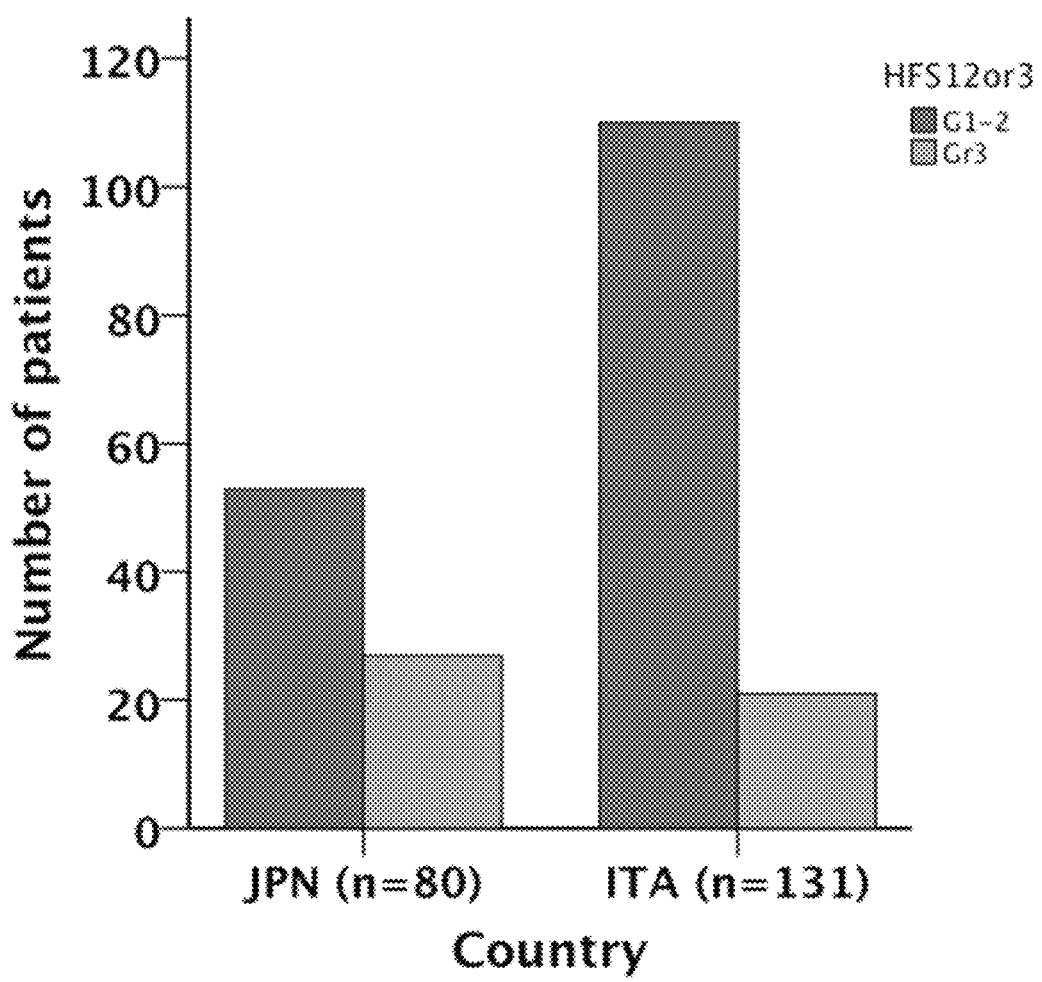
FIG. 1 illustrates data for the difference in HFSR frequency experienced by patients receiving regorafenib treatment in Japan compared to Italy.
Figure 2:
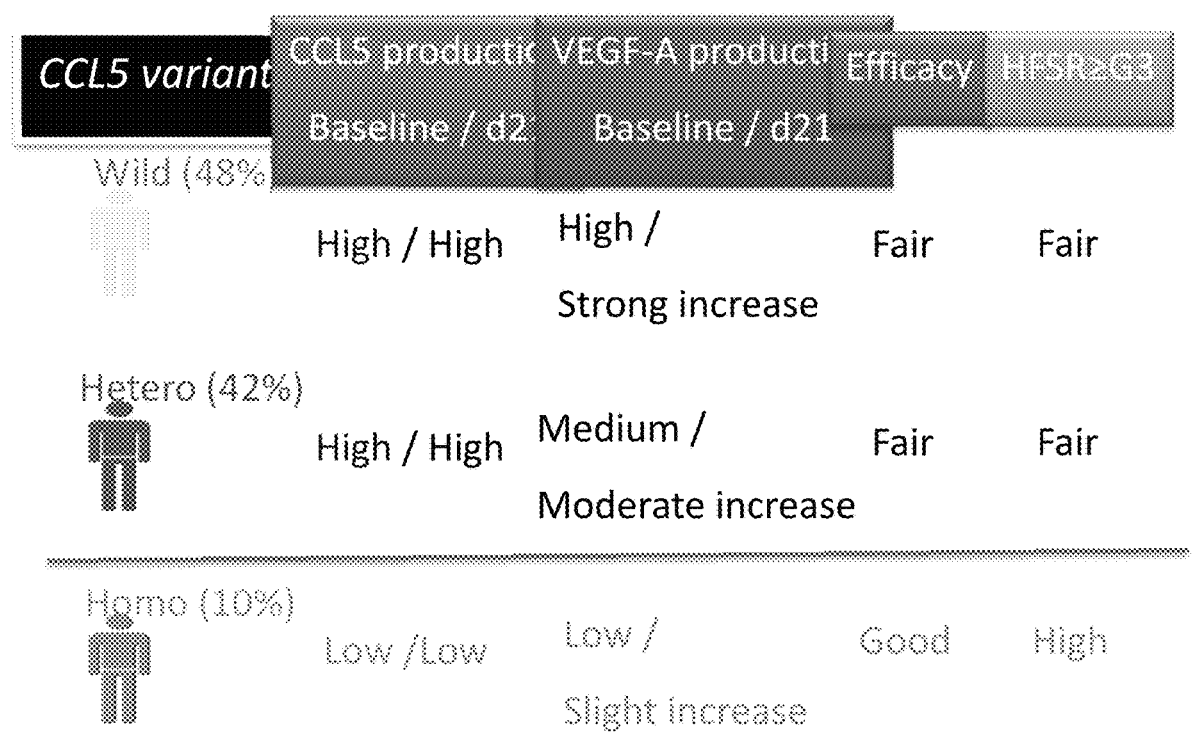
FIG. 2 illustrates data for correlation of CCL5 variants with CCL5 concentration and VEGF-A concentration in blood on various days following regorafenib treatment.
Figure 3:
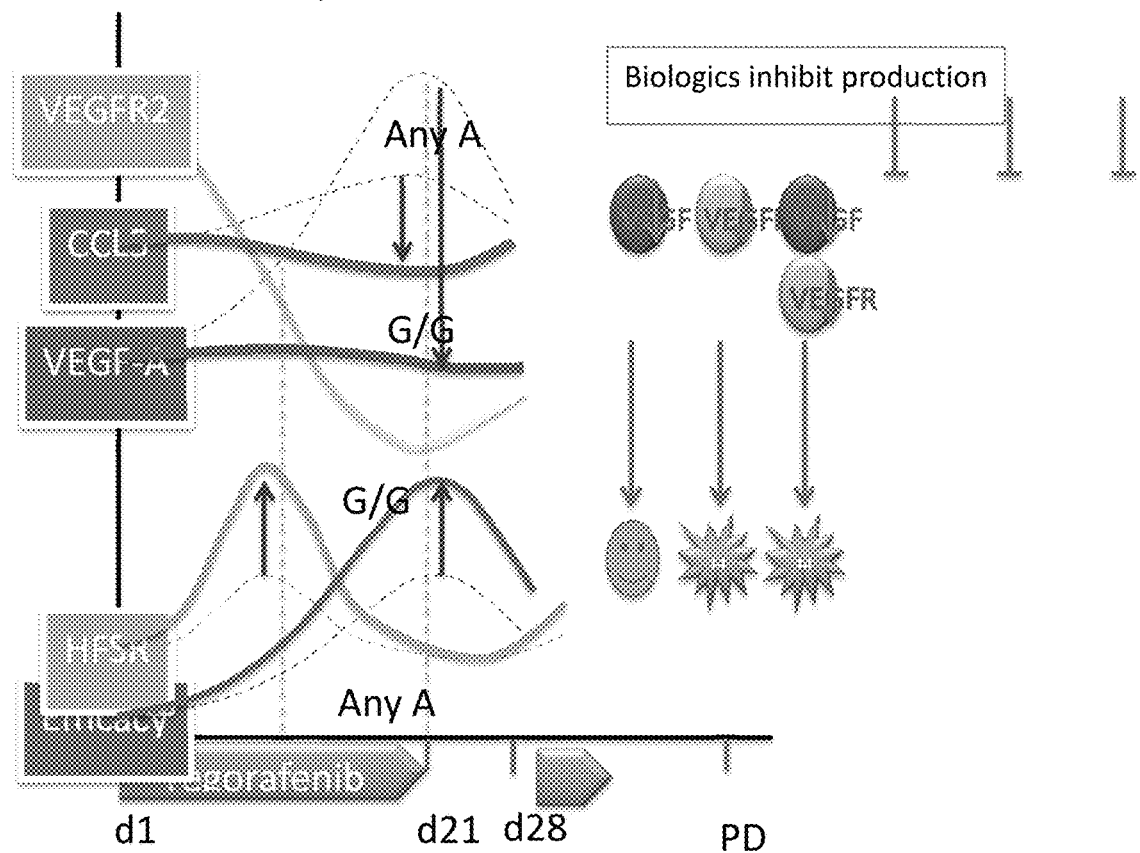
FIG. 3 illustrates data for correlation of CCL5 variants with CCL5, VEGFR2, and VEGF-A concentration in blood on various days following regorafenib treatment.

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "therapy" is synonymous with term "chemotherapy" that encompasses cancer therapies that employ chemical or biological agents or other therapies, such as radiation therapies, e.g., a small molecule drug or a large molecule, such as antibodies, RNAi and gene therapies. Non-limiting examples of chemotherapies are provided below. Unless specifically excluded, when a specific therapy is recited, equivalents of the therapy are within the scope of this invention.

Regorafenib (BAY 73-4506) is sold under the trade name of Stivarga® by Bayer AG. It is an oral anti-cancer and anti-angiogenic agent that possesses various activities including inhibitory activity on multikinases including (VEGFR)-1,-2, and -3, FGFR-1, PDFR-α/β and ret, c-Kit, raf-1 signalling molecules. The molecular formula is C2'1H15CIF4N4O3, and the chemical name is 4-O-(3-(4-Chloro-3-(trifluoromethyl)phenyl)ureido)-3-fluorophenoxy)-N-methylpicolinamide. The two dimensional structure is:

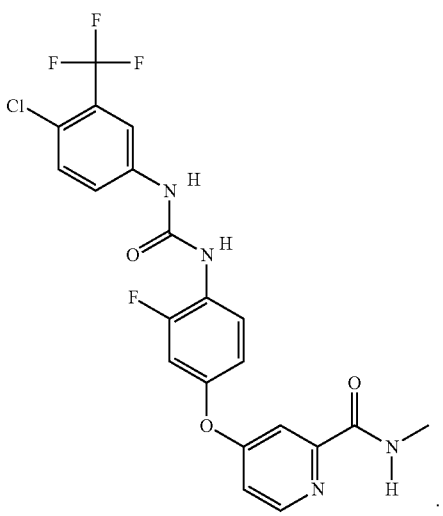

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at cancer.gov. Typically, a patient is given a subsequent chemotherapy regimen because the patient did not shown a positive clinical or sub-clinical response to the first line therapy or the first line therapy has stopped.

In one aspect, the term "equivalent" or "biological equivalent" of an antibody means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

In one aspect, the term "equivalent" of "chemical equivalent" of a chemical means the ability of the chemical to selectively interact with its target protein, DNA, RNA or fragment thereof as measured by the inactivation of the target protein, incorporation of the chemical into the DNA or RNA or other suitable methods. Chemical equivalents include, but are not limited to, those agents with the same or similar biological activity and include, without limitation a pharmaceutically acceptable salt or mixtures thereof that interact with and/or inactivate the same target protein, DNA, or RNA as the reference chemical.

The term "allele," which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

As used herein, the term "determining the genotype of a cell or tissue sample" intends to identify the genotypes of polymorphic loci of interest in the cell or tissue sample. In one aspect, a polymorphic locus is a single nucleotide polymorphic (SNP) locus. If the allelic composition of a SNP locus is heterozygous, the genotype of the SNP locus will be identified as "X/Y" wherein X and Y are two different nucleotides. If the allelic composition of a SNP locus is heterozygous, the genotype of the SNP locus will be identified as "X/X" wherein X identifies the nucleotide that is present at both alleles.

The term "genetic marker" refers to an allelic variant of a polymorphic region of a gene of interest and/or the expression level of a gene of interest.

The term "polymorphism" refers to the coexistence of more than one form of a gene or portion thereof. A portion of a gene of which there are at least two different forms, i.e., two different nucleotide sequences, is referred to as a "polymorphic region of a gene." A polymorphic region can be a single nucleotide, the identity of which differs in different alleles.

The term "genotype" refers to the specific allelic composition of an entire cell or a certain gene and in some aspects a specific polymorphism associated with that gene, whereas the term "phenotype" refers to the detectable outward manifestations of a specific genotype.

The terms "KRAS wild-type" and "BRAF wild-type" refers to a genotype of a cell or patient in which no mutation is detected in the corresponding gene. In some aspects, no mutation is detected that affects the function or activity of the gene.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "isolated" as used herein refers to molecules or biological or cellular materials being substantially free from other materials. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

The term "treating" as used herein is intended to encompass curing as well as ameliorating at least one symptom of the condition or disease. For example, in the case of cancer, a response to treatment includes a reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival, overall survival, each as measured by standards set by the National Cancer Institute and the U.S. Food and Drug Administration for the approval of new drugs.

"An effective amount" or "therapeutically effect amount" intends to indicate the amount of a compound or agent administered or delivered to the patient which is most likely to result in the desired response to treatment. The amount is empirically determined by the patient's clinical parameters including, but not limited to the Stage of disease, age, gender, histology, and likelihood for tumor recurrence.

A "patient" as used herein intends an animal patient, a mammal patient or yet further a human patient. For the purpose of illustration only, a mammal includes but is not limited to a simian, a murine, a bovine, an equine, a porcine or an ovine subject.

The term "clinical outcome", "clinical parameter", "clinical response", or "clinical endpoint" refers to any clinical observation or measurement relating to a patient's reaction to a therapy. Non-limiting examples of clinical outcomes include tumor response (TR), overall survival (OS), progression free survival (PFS), disease free survival, time to tumor recurrence (TTR), time to tumor progression (TTP), relative risk (RR), toxicity or side effect.

The term "HFSR" refers to hand foot skin reaction, which is a major complication associated with a therapy comprising an administration of regorafenib or an equivalent thereof. HFSR are reported as the most common adverse reaction of a grade of 3-4 or higher induced by regorafenib therapy. Toxicity manifested as HFSR affects a favorable clinical outcome of regorafenib therapy and warrants management strategies therefor.

The term "suitable for a therapy" or "suitably treated with a therapy" shall mean that the patient is likely to exhibit one or more desirable clinical outcomes as compared to patients having the same disease and receiving the same therapy but possessing a different characteristic that is under consideration for the purpose of the comparison. In one aspect, the characteristic under consideration is a genetic polymorphism or a somatic mutation. In another aspect, the characteristic under consideration is expression level of a gene or a polypeptide. In one aspect, a more desirable clinical outcome is relatively higher likelihood of or relatively better tumor response such as tumor load reduction. In another aspect, a more desirable clinical outcome is relatively longer overall survival. In yet another aspect, a more desirable clinical outcome is relatively longer progression free survival or time to tumor progression. In yet another aspect, a more desirable clinical outcome is relatively longer disease free survival. In further another aspect, a more desirable clinical outcome is relative reduction or delay in tumor recurrence. In another aspect, a more desirable clinical outcome is relatively decreased metastasis. In another aspect, a more desirable clinical outcome is relatively lower relative risk. In yet another aspect, a more desirable clinical outcome is relatively reduced toxicity or side effects. In some embodiments, more than one clinical outcomes are considered simultaneously. In one such aspect, a patient possessing a characteristic, such as a genotype of a genetic polymorphism, can exhibit more than one more desirable clinical outcomes as compared to patients having the same disease and receiving the same therapy but not possessing the characteristic. As defined herein, the patient is considered suitable for the therapy. In another such aspect, a patient possessing a characteristic can exhibit one or more desirable clinical outcome but simultaneously exhibit one or more less desirable clinical outcome. The clinical outcomes will then be considered collectively, and a decision as to whether the patient is suitable for the therapy will be made accordingly, taking into account the patient's specific situation and the relevance of the clinical outcomes. In some embodiments, progression free survival or overall survival is weighted more heavily than tumor response in a collective decision making.

A "complete response" (CR) to a therapy refers to the clinical status of a patient with evaluable but non-measurable disease, whose tumor and all evidence of disease have disappeared following administration of the therapy. In this context, a "partial response" (PR) refers to a response that is anything less than a complete response. "Stable disease" (SD) indicates that the patient is stable following the therapy. "Progressive disease" (PD) indicates that the tumor has grown (i.e. become larger) or spread (i.e. metastasized to another tissue or organ) or the overall cancer has gotten worse following the therapy. For example, tumor growth of more than 20 percent since the start of therapy typically indicates progressive disease. "Non-response" (NR) to a therapy refers to status of a patient whose tumor or evidence of disease has remained constant or has progressed.

"Overall Survival" (OS) refers to the length of time of a cancer patient remaining alive following a cancer therapy.

"Progression free survival" (PFS) or "Time to Tumor Progression" (TTP) refers to the length of time following a therapy, during which the tumor in a cancer patient does not grow. Progression-free survival includes the amount of time a patient has experienced a complete response, partial response or stable disease.

"Disease free survival" refers to the length of time following a therapy, during which a cancer patient survives with no signs of the cancer or tumor.

"Time to Tumor Recurrence (TTR)" refers to the length of time, following a cancer therapy such as surgical resection or chemotherapy, until the tumor has reappeared (come back). The tumor may come back to the same place as the original (primary) tumor or to another place in the body.

"Relative Risk" (RR), in statistics and mathematical epidemiology, refers to the risk of an event (or of developing a disease) relative to exposure. Relative risk is a ratio of the probability of the event occurring in the exposed group versus a non-exposed group.

The term "identify" or "identifying" is to associate or affiliate a patient closely to a group or population of patients who likely experience the same or a similar clinical response to a therapy.

The term "selecting" a patient for a therapy refers to making an indication that the selected patient is suitable for the therapy. Such an indication can be made in writing by, for instance, a handwritten prescription or a computerized report making the corresponding prescription or recommendation.

The term "determining" refers to making an indication that the determined patient is likely or not likely to experience complication or reactions from an administered cancer therapy. Such an indication can be made in writing by, for instance, a handwritten document or a computerized report making the corresponding therapy management decisions or strategies.

When a genetic marker or polymorphism "is used as a basis" for identifying or selecting a patient for a treatment described herein, the genetic marker or polymorphism is measured before and/or during treatment, and the values obtained are used by a clinician in assessing any of the following: (a) probable or likely suitability of an individual to initially receive treatment(s); (b) probable or likely unsuitability of an individual to initially receive treatment (s); (c) responsiveness to treatment; (d) probable or likely suitability of an individual to continue to receive treatment (s); (e) probable or likely unsuitability of an individual to continue to receive treatment(s); (f) adjusting dosage; (g) predicting likelihood of clinical benefits; or (h) toxicity. As would be well understood by one in the art, measurement of the genetic marker or polymorphism in a clinical setting is a clear indication that this parameter was used as a basis for initiating, continuing, adjusting and/or ceasing administration of the treatments described herein.

"Having the same cancer" is used when comparing one patient to another or alternatively, one patient population to another patient population. For example, the two patients or patient population will each have or be suffering from colon cancer.

A "normal cell corresponding to the tumor tissue type" refers to a normal cell from a same tissue type as the tumor tissue. A non-limiting examples is a normal lung cell from a patient having lung tumor, or a normal colon cell from a patient having colon tumor.

The term "amplification" or "amplify" as used herein means one or more methods known in the art for copying a target nucleic acid, thereby increasing the number of copies of a selected nucleic acid sequence. Amplification can be exponential or linear. A target nucleic acid can be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods can be used either in place of, or together with, PCR methods.

The term "complement" as used herein means the complementary sequence to a nucleic acid according to standard Watson/Crick base pairing rules. A complement sequence can also be a sequence of RNA complementary to the DNA sequence or its complement sequence, and can also be a cDNA. The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

As used herein, the term "hybridize" or "specifically hybridize" refers to a process where two complementary nucleic acid strands anneal to each other under appropriately stringent conditions. Hybridizations are typically conducted with probe-length nucleic acid molecules. Nucleic acid hybridization techniques are well known in the art. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

"Primer" as used herein refers to an oligonucleotide that is capable of acting as a point of initiation of synthesis when placed under conditions in which primer extension is initiated (e.g., primer extension associated with an application such as PCR). The primer is complementary to a target nucleotide sequence and it hybridizes to a substantially complementary sequence in the target and leads to addition of nucleotides to the 3'-end of the primer in the presence of a DNA or RNA polymerase. The 3'-nucleotide of the primer should generally be complementary to the target sequence at a corresponding nucleotide position for optimal expression and amplification. An oligonucleotide "primer" can occur naturally, as in a purified restriction digest or can be produced synthetically. The term "primer" as used herein includes all forms of primers that can be synthesized including, peptide nucleic acid primers, locked nucleic acid primers, phosphorothioate modified primers, labeled primers, and the like.

Primers are typically between about 5 and about 100 nucleotides in length, such as between about 15 and about 60 nucleotides in length, such as between about 20 and about 50 nucleotides in length, such as between about 25 and about 40 nucleotides in length. In some embodiments, primers can be at least 8, at least 12, at least 16, at least 20, at least 25, at least 30, at least 35, at least 40, at least 45, at least 50, at least 55, at least 60 nucleotides in length. An optimal length for a particular primer application can be readily determined in the manner described in H. Erlich, PCR Technology. Principles and Application for DNA Amplification (1989).

"Probe" as used herein refers to nucleic acid that interacts with a target nucleic acid via hybridization. A probe can be fully complementary to a target nucleic acid sequence or partially complementary. The level of complementarity will depend on many factors based, in general, on the function of the probe. A probe or probes can be used, for example to detect the presence or absence of a mutation in a nucleic acid sequence by virtue of the sequence characteristics of the target. Probes can be labeled or unlabeled, or modified in any of a number of ways well known in the art. A probe can specifically hybridize to a target nucleic acid.

Probes can be DNA, RNA or a RNA/DNA hybrid. Probes can be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes can comprise modified nucleobases, modified sugar moieties, and modified internucleotide linkages. A probe can be fully complementary to a target nucleic acid sequence or partially complementary. A probe can be used to detect the presence or absence of a target nucleic acid. Probes are typically at least about 10, 15, 21, 25, 30, 35, 40, 50, 60, 75, 100 nucleotides or more in length.

"Detecting" as used herein refers to determining the presence of a nucleic acid of interest in a sample or the presence of a protein of interest in a sample. Detection does not require the method to provide 100% sensitivity and/or 100% specificity.

"Detectable label" as used herein refers to a molecule or a compound or a group of molecules or a group of compounds used to identify a nucleic acid or protein of interest.

In some cases, the detectable label can be detected directly. In other cases, the detectable label can be a part of a binding pair, which can then be subsequently detected. Signals from the detectable label can be detected by various means and will depend on the nature of the detectable label. Detectable labels can be isotopes, fluorescent moieties, colored substances, and the like. Examples of means to detect detectable label include but are not limited to spectroscopic, photochemical, biochemical, immunochemical, electromagnetic, radiochemical, or chemical means, such as fluorescence, chemifluorescence, or chemiluminescence, or any other appropriate means.

"TaqMan® PCR detection system" as used herein refers to a method for real time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

As used herein, the term "sample" or "test sample" refers to any liquid or solid material containing nucleic acids. In suitable embodiments, a test sample is obtained from a biological source (i.e., a "biological sample"), such as cells in culture or a tissue sample from an animal, preferably, a human. In an exemplary embodiment, the sample is a biopsy sample.

"Target nucleic acid" as used herein refers to segments of a chromosome, a complete gene with or without intergenic sequence, segments or portions a gene with or without intergenic sequence, or sequence of nucleic acids to which probes or primers are designed. Target nucleic acids can include wild type sequences, nucleic acid sequences containing mutations, deletions or duplications, tandem repeat regions, a gene of interest, a region of a gene of interest or any upstream or downstream region thereof. Target nucleic acids can represent alternative sequences or alleles of a particular gene. Target nucleic acids can be derived from genomic DNA, cDNA, or RNA. As used herein, target nucleic acid can be native DNA or a PCR-amplified product.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have sufficiently long segments with a high frequency of complementary base sequences. Exemplary hybridization conditions are as follows. High stringency generally refers to conditions that permit hybridization of only those nucleic acid sequences that form stable hybrids in 0.018 M NaCl at 65° C. High stringency conditions can be provided, for example, by hybridization in 50% formamide, 5×Denhardt's solution, 5×SSC (saline sodium citrate) 0.2% SDS (sodium dodecyl sulfate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2×SSC, 0.2% SDS, at 65° C. Low stringency refers to conditions equivalent to hybridization in 10% formamide, 5×Denhardt's solution, 6×SSC, 0.2% SDS, followed by washing in 1° SSC, 0.2% SDS, at 50° C.

As used herein the term "substantially identical" refers to a polypeptide or nucleic acid exhibiting at least 50%, 75%, 85%, 90%, 95%, or even 99% identity to a reference amino acid or nucleic acid sequence over the region of comparison. For polypeptides, the length of comparison sequences will generally be at least 20, 30, 40, or 50 amino acids or more, or the full length of the polypeptide. For nucleic acids, the length of comparison sequences will generally be at least 10, 15, 20, 25, 30, 40, 50, 75, or 100 nucleotides or more, or the full length of the nucleic acid.

Descriptive Embodiments

The disclosure further provides diagnostic, prognostic and therapeutic methods, which are based, at least in part, on determination of the identify of a genotype of interest identified herein.

For example, information obtained using the diagnostic assays described herein is useful for determining if a subject is suitable for cancer treatment of a given type. Based on the prognostic information, a doctor can recommend a therapeutic protocol, useful for reducing the malignant mass or tumor in the patient or treat cancer in the individual.

A patient's likely clinical outcome following a clinical procedure such as a therapy or surgery can be expressed in relative terms. For example, a patient having a particular genotype or expression level can experience relatively longer overall survival than a patient or patients not having the genotype or expression level. The patient having the particular genotype or expression level, alternatively, can be considered as likely to survive. Similarly, a patient having a particular genotype or expression level can experience relatively longer progression free survival, or time to tumor progression, than a patient or patients not having the genotype or expression level. The patient having the particular genotype or expression level, alternatively, can be considered as not likely to suffer tumor progression. Further, a patient having a particular genotype or expression level can experience relatively shorter time to tumor recurrence than a patient or patients not having the genotype or expression level. The patient having the particular genotype or expression level, alternatively, can be considered as not likely to suffer tumor recurrence. Yet in another example, a patient having a particular genotype or expression level can experience relatively more complete response or partial response than a patient or patients not having the genotype or expression level. The patient having the particular genotype or expression level, alternatively, can be considered as likely to respond. Accordingly, a patient that is likely to survive, or not likely to suffer tumor progression, or not likely to suffer tumor recurrence, or likely to respond following a clinical procedure is considered suitable for the clinical procedure.

It is to be understood that information obtained using the diagnostic assays described herein can be used alone or in combination with other information, such as, but not limited to, genotypes or expression levels of other genes, clinical chemical parameters, histopathological parameters, or age, gender and weight of the subject. When used alone, the information obtained using the diagnostic assays described herein is useful in determining or identifying the clinical outcome of a treatment, selecting a patient for a treatment, or treating a patient, etc. When used in combination with other information, on the other hand, the information obtained using the diagnostic assays described herein is useful in aiding in the determination or identification of clinical outcome of a treatment, aiding in the selection of a patient for a treatment, or aiding in the treatment of a patient and etc. In a particular aspect, the genotypes or expression levels of one or more genes as disclosed herein are used in a panel of genes, each of which contributes to the final diagnosis, prognosis or treatment.

The methods are useful in the assistance of an animal, a mammal or yet further a human patient. For the purpose of illustration only, a mammal includes but is not limited to a human, a simian, a murine, a bovine, an equine, a porcine or an ovine subject.

Diagnostic Methods

Provided, in one embodiment, is a method for determining whether a cancer patient is likely or not likely to experience HFSR (hand foot skin reaction) from a therapy comprising administration of an effective amount of regorafenib or an equivalent thereof, comprising screening a biological sample isolated from the patient for the rs2280789 polymorphism and/or the rs3817655 polymorphism, and determining that the patient is likely to experience HFSR if the genotype of (G/G) for the rs2280789, or (G/G) for rs3817655 is present in the sample; and that the patient is not likely to experience HFSR if the genotype of (G/G) is absent in the sample. In some aspects, the patient is determined likely to experience HFSR if the genotype of (G/G) for the rs2280789 or (G/G) for rs3817655 is not present in the sample. In some aspects, the patient is determined not likely to experience HFSR if the genotype of (A/A) or (G/A) for the rs2280789, or (A/A) or (G/A) for rs3817655 is present in the sample.

Also provided, in one embodiment, is a method for selecting a cancer patient for a therapy comprising regorafenib or an equivalent thereof, comprising screening a biological sample isolated from the patient for the rs7527092 polymorphism, and/or rs2071559 polymorphism, and/or the combination of rs2071559 and rs6563 and rs2442599, and/or the combination of rs7527092 and rs2268614, and/or the combination of rs2071559 and rs3125001 and rs2916702, and selecting the patient for the therapy if the genotype of (A/G) or (G/G) for the rs7527092, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 is present in the sample. In some aspects, the patient is not selected for the therapy if the genotype of (A/G) or (G/G) for the rs7527092, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 is not present in the sample. In some aspects, the patient is not selected for the therapy if the genotype of (A/A) for the rs7527092, or (G/G) for the rs2071559, or (G/G) for the rs2071559 and (A/A) for the rs6563 and (A/A) for the rs2442599, or (A/A) for the rs7527092 and (C/C) for the rs2268614, or (G/G) for the rs2071559 and (T/C) or (T/T) for the rs3125001 and (G/G) for the rs2916702 is present in the sample. In some embodiments, the patient is selected for a regorafenib-free and/or a regorafenib-equivalent-free therapy if the genotype of (A/G) or (G/G) for the rs7527092, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 is not present in the sample. In some embodiments, the patient is selected for a regorafenib-free and/or a regorafenib-equivalent-free if the genotype of (A/A) for the rs7527092, or (G/G) for the rs2071559, or (G/G) for the rs2071559 and (A/A) for the rs6563 and (A/A) for the rs2442599, or (A/A) for the rs7527092 and (C/C) for the rs2268614, or (G/G) for the rs2071559 and (T/C) or (T/T) for the rs3125001 and (G/G) for the rs2916702 is present in the sample.

Also further provided is a method for identifying whether a cancer patient is likely to experience a relatively longer or shorter progression free survival following a therapy comprising regorafenib or an equivalent thereof, comprising screening a biological sample isolated from the patient for the rs2071559 and/or the combination of rs2071559 and rs6563 and rs2442599 polymorphism, and identifying that the patient is likely to experience a longer progression free survival if the genotype of (G/A) or (A/A) for the rs2071559, or (G/G) for the rs2071559 and (A/G) or (G/G) for the rs6563 and (A/G) or (G/G) for the rs2442599 is present in the sample, relative to a cancer patient not having the genotype.

In some aspects, the patient suffers from colorectal cancer or gastrointestinal stromal cancer. In some aspects, the colorectal cancer is non-metastatic colorectal cancer or metastatic colorectal cancer. In some aspects, the colorectal cancer is metastatic or non-metastatic colon cancer. In some aspects, the colorectal cancer is metastatic or non-metastatic rectal cancer. In some aspects, the gastrointestinal stromal cancer is non-metastatic or metastatic gastrointestinal stromal cancer.

Any suitable method for identifying the genotype in the patient sample can be used and the disclosures described herein are not to be limited to these methods. For the purpose of illustration only, the genotype is determined by a method comprising, or alternatively consisting essentially of, or yet further consisting of, sequencing, hybridization, nucleic acid amplification, including polymerase chain reaction (PCR), real-time PCR, reverse transcriptase PCR (RT-PCR), nested PCR, ligase chain reaction, or PCR-RFLP, or microarray. These methods as well as equivalents or alternatives thereto are described herein.

The methods are useful in the assistance of an animal, a mammal or yet further a human patient. For the purpose of illustration only, a mammal includes but is not limited to a human, a simian, a murine, a bovine, an equine, a porcine or an ovine subject.

Information obtained using the diagnostic assays described herein is useful for determining if a subject will likely, more likely, or less likely to respond to cancer treatment of a given type. Based on the prognostic information, a doctor can recommend a therapeutic protocol, useful for treating reducing the malignant mass or tumor in the patient or treat cancer in the individual.

In addition, knowledge of the identity of a particular allele in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. The identity of the genotype or expression patterns of individual patients can then be compared to the genotype or expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

Biological Sample Collection and Preparation

The methods and compositions disclosed herein can be used to detect nucleic acids associated with a the rs2280789 polymorphism, the rs3817655 polymorphism, rs7527092 polymorphism, and/or rs2071559 polymorphism, and/or the combination of rs2071559 and rs6563 and rs2442599, and/or the combination of rs7527092 and rs2268614, and/or the combination of rs2071559 and rs3125001 and rs2916702 using a biological sample obtained from a patient. Biological samples can be obtained by standard procedures and can be used immediately or stored, under conditions appropriate for the type of biological sample, for later use. Any liquid or solid biological material obtained from the patient believed to contain nucleic acids comprising the region containing rs2280789 polymorphism, the rs3817655 polymorphism, rs7527092 polymorphism, and/or rs2071559 polymorphism, and/or the combination of rs2071559 and rs6563 and rs2442599, and/or the combination of rs7527092 and rs2268614, and/or the combination of rs2071559 and rs3125001 and rs2916702 can be an suitable sample.

Methods of obtaining test samples are known to those of skill in the art and include, but are not limited to, aspirations, tissue sections, swabs, drawing of blood or other fluids, surgical or needle biopsies.

In some aspects, the biological sample is a tissue or a cell sample. Suitable patient samples in the methods include, but are not limited to, blood, plasma, serum, a biopsy tissue, fine needle biopsy sample, amniotic fluid, plasma, pleural fluid, saliva, semen, serum, tissue or tissue homogenates, frozen or paraffin sections of tissue or combinations thereof. In some aspects, the biological sample comprises, or alternatively consisting essentially of, or yet further consisting of, at least one of a tumor cell, a normal cell adjacent to a tumor, a normal cell corresponding to the tumor tissue type, a blood cell, a peripheral blood lymphocyte, or combinations thereof. In some aspects, the biological sample is an original sample recently isolated from the patient, a fixed tissue, a frozen tissue, a resection tissue, or a microdissected tissue. In some aspects, the biological samples are processed, such as by sectioning of tissues, fractionation, purification, nucleic acid isolation, or cellular organelle separation.

In some embodiments, nucleic acid (DNA or RNA) is isolated from the sample according to any methods known to those of skill in the art. In some aspects, genomic DNA is isolated from the biological sample. In some aspects, RNA is isolated from the biological sample. In some aspects, cDNA is generated from mRNA in the sample. In some embodiments, the nucleic acid is not isolated from the biological sample (e.g., the polymorphism is detected directly from the biological sample).

Detection of Polymorphisms

In some aspects, detection of polymorphisms can be accomplished by molecular cloning of the specified allele and subsequent sequencing of that allele using techniques known in the art, in some aspects, after isolation of a suitable nucleic acid sample. In some aspects, the gene sequences can be amplified directly from a genomic DNA preparation from the biological sample using PCR, and the sequence composition is determined by sequencing the amplified product (i.e., amplicon). Alternatively, the PCR product can be analyzed following digestion with a restriction enzyme, a method known as PCR-RFLP.

In some embodiments, the polymorphism is detected using allele specific hybridization using probes overlapping the polymorphic site. In some aspects, the nucleic acid probes are between 5 and 40 nucleotides in length. In some aspects, the nucleic acid probes are about 5, about 10, about 15, about 20, about 25, about 30, about 35, or about 40 or more nucleotides flanking the polymorphic site. For example, in some embodiments, the nucleic acid specifically binds to a nucleic acid having the sequence of any of SEQ ID NO: 1-2 and overlaps the polymorphic site. In some embodiments, the nucleic acid specifically binds to a nucleic acid having the sequence of any of SEQ ID NO: 7-8 and overlaps the polymorphic site. Exemplary probes include nucleic acid probes having about 5, about 10, about 15, about 20, about 25, about 30, about 35, about 40 or more contiguous nucleotides of any of SEQ ID NO: 1-2 and overlaps the polymorphic site. Exemplary probes also include nucleic acid probes having about 5, about 10, about 15, about 20, about 25, about 30, about 35, about 40 or more contiguous nucleotides of any of SEQ ID NO: 7-8 and overlaps the polymorphic site.

In some embodiments, the combination of polymorphisms is detected using allele specific hybridization using multiple probes overlapping the polymorphic site of each of the individual polymorphism from the combination respectively. In some aspects, the nucleic acid probes are between 5 and 40 nucleotides in length. In some aspects, the nucleic acid probes are about 5, about 10, about 15, about 20, about 25, about 30, about 35, or about 40 or more nucleotides flanking the polymorphic site. For example, in some embodiments, the nucleic acid specifically binds to a nucleic acid having the sequence of SEQ ID NO: 8 and overlaps the polymorphic site. In some embodiments, the nucleic acid specifically binds to a nucleic acid having the sequence of SEQ ID NO: 15 and overlaps the polymorphic site. In some embodiments, the nucleic acid specifically binds to a nucleic acid having the sequence of SEQ ID NO: 13 and overlaps the polymorphic site. In some embodiments, the nucleic acid specifically binds to a nucleic acid having the sequence of SEQ ID NO: 7 and overlaps the polymorphic site. In some embodiments, the nucleic acid specifically binds to a nucleic acid having the sequence of SEQ ID NO: 17 and overlaps the polymorphic site. In some embodiments, the nucleic acid specifically binds to a nucleic acid having the sequence of SEQ ID NO: 8 and overlaps the polymorphic site. In some embodiments, the nucleic acid specifically binds to a nucleic acid having the sequence of SEQ ID NO: 16 and overlaps the polymorphic site. In some embodiments, the nucleic acid specifically binds to a nucleic acid having the sequence of SEQ ID NO: 14 and overlaps the polymorphic site.

In another embodiment of the disclosure, several nucleic acid probes capable of hybridizing specifically to the nucleic acid containing the allelic variant are attached to a solid phase support, e.g., a "chip" or "microarray. Such gene chips or microarrays can be used to detect genetic variations by a number of techniques known to one of skill in the art. In one technique, oligonucleotides are arrayed on a gene chip for determining the DNA sequence by the sequencing by hybridization approach. The probes of the disclosure also can be used for fluorescent detection of a genetic sequence. A probe also can be affixed to an electrode surface for the electrochemical detection of nucleic acid sequences.

In one aspect, "gene chips" or "microarrays" containing probes or primers for the gene of interest are provided alone or in combination with other probes and/or primers. A suitable sample is obtained from the patient extraction of genomic DNA, RNA, or any combination thereof and amplified if necessary. The DNA or RNA sample is contacted to the gene chip or microarray panel under conditions suitable for hybridization of the gene(s) of interest to the probe(s) or primer(s) contained on the gene chip or microarray. The probes or primers can be detectably labeled thereby identifying the polymorphism in the gene(s) of interest. Alternatively, a chemical or biological reaction can be used to identify the probes or primers which hybridized with the DNA or RNA of the gene(s) of interest. The genetic profile of the patient is then determined with the aid of the aforementioned apparatus and methods.

In some aspects, whole genome sequencing, in particular with the "next generation sequencing" techniques, which employ massively parallel sequencing of DNA templates, can be used to obtain genotypes of relevant polymorphisms. Exemplary NGS sequencing platforms for the generation of nucleic acid sequence data include, but are not limited to, Illumina's sequencing by synthesis technology (e.g., Illumina MiSeq or HiSeq System), Life Technologies' Ion Torrent semiconductor sequencing technology (e.g., Ion Torrent PGM or Proton system), the Roche (454 Life Sciences) GS series and Qiagen (Intelligent BioSystems) Gene Reader sequencing platforms.

In some aspects, nucleic acid comprising the polymorphism is amplified to produce an amplicon containing the polymorphism. Nucleic acids can be amplified by various methods known to the skilled artisan. Nucleic acid amplification can be linear or exponential. Amplification is generally carried out using polymerase chain reaction (PCR) technologies. Alternative or modified PCR amplification methods can also be used and include, for example, isothermal amplification methods, rolling circle methods, Hot-start PCR, real-time PCR, Allele-specific PCR, Assembly PCR or Polymerase Cycling Assembly (PCA), Asymmetric PCR, Colony PCR, Emulsion PCR, Fast PCR, Real-Time PCR, nucleic acid ligation, Gap Ligation Chain Reaction (Gap LCR), Ligation-mediated PCR, Multiplex Ligation-dependent Probe Amplification, (MLPA), Gap Extension Ligation PCR (GEXL-PCR), quantitative PCR (Q-PCR), Quantitative real-time PCR (QRT-PCR), multiplex PCR, Helicase-dependent amplification, Intersequence-specific (ISSR) PCR, Inverse PCR, Linear-After-The-Exponential-PCR (LATE-PCR), Methylation-specific PCR (MSP), Nested PCR, Overlap-extension PCR, PAN-AC assay, Reverse Transcription PCR(RT-PCR), Rapid Amplification of cDNA Ends (RACE PCR), Single molecule amplification PCR (SMA PCR), Thermal asymmetric interlaced PCR (TAIL-PCR), Touchdown PCR, long PCR, nucleic acid sequencing (including DNA sequencing and RNA sequencing), transcription, reverse transcription, duplication, DNA or RNA ligation, and other nucleic acid extension reactions known in the art. The skilled artisan will understand that other methods can be used either in place of, or together with, PCR methods, including enzymatic replication reactions developed in the future. See, e.g., Saiki, "Amplification of Genomic DNA" in *PCR Protocols*, Innis et al., eds., Academic Press, San Diego, Calif., 13-20 (1990); Wharam, et al., 29(11) *Nucleic Acids Res*, E54-E54 (2001); Hafner, et al., 30(4) *Biotechniques,* 852-6, 858, 860 passim (2001).

In some aspects, nucleic acid comprising the rs2280789 polymorphism, and/or the rs3817655 polymorphism is amplified to produce an amplicon containing the rs2280789 polymorphism, and/or the rs3817655. For example, in some aspects, nucleic acid comprising SEQ ID NO: 1, or 2 is amplified to generate an amplicon comprising any of SEQ ID NO: 1, or 2, respectively. In some aspects, nucleic acid containing the rs2280789, and/or the rs3817655 polymorphism is amplified using a forward primer and a reverse primer the flank the rs2280789, and/or the rs3817655 polymorphism. For example, nucleic acid containing the rs2280789 polymorphism is amplified using a forward primer comprising nucleic acid having the sequence of SEQ ID NO: 3 and a reverse primer comprising nucleic acid having the sequence of SEQ ID NO: 4, and/or nucleic acid containing the rs3817655 polymorphism is amplified using a forward primer comprising nucleic acid having the sequence of SEQ ID NO: 5 and a reverse primer comprising nucleic acid having the sequence of SEQ ID NO: 6. In some aspects, the amplicon containing the rs2280789, and/or the rs3817655 polymorphism is detected using a nucleic acid probe. In some aspects, the amplicon containing the rs2280789, and/or the rs3817655 polymorphism is detected by hybridizing a nucleic acid probe containing the rs2280789, and/or the rs3817655 polymorphism or a complement thereof to the corresponding complementary strand of the amplicon and detecting the hybrid formed between the nucleic acid probe and the complementary strand of the amplicon. In some aspects, amplicon containing the rs2280789, and/or the rs3817655 polymorphism is sequenced (e.g., dideoxy chain termination methods (Sanger method and variants thereof), Maxam & Gilbert sequencing, pyrosequencing, exonuclease digestion and next-generation sequencing methods).

In some aspects, nucleic acid comprising the rs7527092 polymorphism, and/or the rs2071559 polymorphism is amplified to produce an amplicon containing the rs7527092, and/or the rs2071559 polymorphism. For example, in some aspects, nucleic acid comprising SEQ ID NO: 7, or 8 is amplified to generate an amplicon comprising any of SEQ ID NO: 7, or 8, respectively. In some aspects, nucleic acid containing the rs7527092, and/or the rs2071559 polymorphism is amplified using a forward primer and a reverse primer the flank the rs7527092, and/or the rs2071559 polymorphism. For example, nucleic acid containing the rs7527092 polymorphism is amplified using a forward primer comprising nucleic acid having the sequence of SEQ ID NO: 9 and a reverse primer comprising nucleic acid having the sequence of SEQ ID NO: 10, and/or nucleic acid containing the rs2071559 polymorphism is amplified using a forward primer comprising nucleic acid having the sequence of SEQ ID NO: 11 and a reverse primer comprising nucleic acid having the sequence of SEQ ID NO: 12. In some aspects, the amplicon containing the rs7527092, and/or the rs2071559 polymorphism is detected using a nucleic acid probe. In some aspects, the amplicon containing the rs7527092, and/or the rs2071559 polymorphism is detected by hybridizing a nucleic acid probe containing the rs7527092, and/or the rs2071559 polymorphism or a complement thereof to the corresponding complementary strand of the amplicon and detecting the hybrid formed between the nucleic acid probe and the complementary strand of the amplicon. In some aspects, amplicon containing the rs7527092, and/or the rs2071559 polymorphism is sequenced (e.g., dideoxy chain termination methods (Sanger method and variants thereof), Maxam & Gilbert sequencing, pyrosequencing, exonuclease digestion and next-generation sequencing methods).

In some aspects, nucleic acids comprising the rs2071559 and rs6563 and rs2442599 polymorphism are amplified to produce amplicons containing the rs2071559 and rs6563 and rs2442599 polymorphism. For example, in some aspects, nucleic acids comprising SEQ ID NO: 8, or 15 or 13 are amplified to generate amplicons comprising any of SEQ ID NO: 8, or 15 or 13, respectively. In some aspects, nucleic acids containing the rs2071559 and rs6563 and rs2442599 polymorphism are amplified using a forward primer and a reverse primer the flank the rs2071559, and/or the rs6563 polymorphism, and/or rs2442599. For example, nucleic acid containing the rs2071559 polymorphism is amplified using a forward primer comprising nucleic acid having the sequence of SEQ ID NO: 11 and a reverse primer comprising nucleic acid having the sequence of SEQ ID NO: 12, and/or nucleic acid containing the rs6563 polymorphism is amplified using a forward primer comprising nucleic acid having the sequence of SEQ ID NO: 18 and a reverse primer comprising nucleic acid having the sequence of SEQ ID NO: 19, and/or nucleic acid containing the rs2442599 polymorphism is amplified using a forward primer comprising nucleic acid having the sequence of SEQ ID NO: 22 and a reverse primer comprising nucleic acid having the sequence of SEQ ID NO: 23. In some aspects, the amplicons containing the rs2071559 and rs6563 and rs2442599 polymorphism are detected using nucleic acid probes. In some aspects, the amplicons containing the rs2071559 and rs6563 and rs2442599 polymorphism are detected by hybridizing nucleic acid probes containing the rs2071559 and rs6563 and rs2442599 polymorphism or a complement thereof to the corresponding complementary strand of the amplicon and detecting the hybrid formed between the nucleic acid probe and the complementary strand of the amplicon. In some aspects, amplicons containing the rs2071559 and rs6563 and rs2442599 polymorphism are sequenced (e.g., dideoxy chain termination methods (Sanger method and variants thereof), Maxam & Gilbert sequencing, pyrosequencing, exonuclease digestion and next-generation sequencing methods).

In some aspects, nucleic acid comprising the combination of rs7527092 and rs2268614 polymorphism is amplified to produce amplicons containing the rs7527092 and rs2268614 polymorphism. For example, in some aspects, nucleic acids comprising SEQ ID NO: 7, or 17 are amplified to generate amplicons comprising any of SEQ ID NO: 7, or 17, respectively. In some aspects, nucleic acids containing the rs7527092 and rs2268614 polymorphism are amplified using a forward primer and a reverse primer the flank the rs7527092 and/or rs2268614. For example, nucleic acid containing the rs7527092 polymorphism is amplified using a forward primer comprising nucleic acid having the sequence of SEQ ID NO: 9 and a reverse primer comprising nucleic acid having the sequence of SEQ ID NO: 10, and/or nucleic acid containing the rs2268614 polymorphism is amplified using a forward primer comprising nucleic acid having the sequence of SEQ ID NO: 26 and a reverse primer comprising nucleic acid having the sequence of SEQ ID NO: 27. In some aspects, the amplicons containing the rs2071559 and rs6563 and rs2442599 polymorphism are detected using nucleic acid probes. In some aspects, the amplicons containing the rs7527092 and rs2268614 polymorphism are detected by hybridizing nucleic acid probes containing the rs7527092 and rs2268614 polymorphism or a complement thereof to the corresponding complementary strand of the amplicon and detecting the hybrid formed between the nucleic acid probe and the complementary strand of the amplicon. In some aspects, amplicons containing the rs7527092 and/or rs2268614 polymorphism are sequenced (e.g., dideoxy chain termination methods (Sanger method and variants thereof), Maxam & Gilbert sequencing, pyrosequencing, exonuclease digestion and next-generation sequencing methods).

In some aspects, nucleic acid comprising the combination of rs2071559 and rs3125001 and rs2916702 polymorphism is amplified to produce amplicons containing the rs2071559 and rs3125001 and rs2916702 polymorphism. For example, in some aspects, nucleic acids comprising SEQ ID NO: 8, or 16 or 14 are amplified to generate amplicons comprising any of SEQ ID NO: 8, or 16 or 14, respectively. In some aspects, nucleic acids containing the rs2071559 and rs3125001 and rs2916702 polymorphism are amplified using a forward primer and a reverse primer the flank the rs2071559 and/or rs3125001 and/or rs2916702 polymorphism, For example, nucleic acid containing the rs2071559 polymorphism is amplified using a forward primer comprising nucleic acid having the sequence of SEQ ID NO: 11 and a reverse primer comprising nucleic acid having the sequence of SEQ ID NO: 12, and/or nucleic acid containing the rs3125001 polymorphism is amplified using a forward primer comprising nucleic acid having the sequence of SEQ ID NO: 20 and a reverse primer comprising nucleic acid having the sequence of SEQ ID NO: 21, and/or nucleic acid containing the rs2916702 polymorphism is amplified using a forward primer comprising nucleic acid having the sequence of SEQ ID NO: 24 and a reverse primer comprising nucleic acid having the sequence of SEQ ID NO: 25, In some aspects, the amplicons containing the rs2071559 and rs3125001 and rs2916702 polymorphism are detected using nucleic acid probes. In some aspects, the amplicons containing the rs2071559 and rs3125001 and rs2916702 polymorphism are detected by hybridizing a nucleic acid probe containing the rs2071559 and rs3125001 and rs2916702 polymorphism or a complement thereof to the corresponding complementary strand of the amplicon and detecting the hybrid formed between the nucleic acid probe and the complementary strand of the amplicon. In some aspects, amplicons containing the rs2071559 and rs3125001 and rs2916702 polymorphism are sequenced (e.g., dideoxy chain termination methods (Sanger method and variants thereof), Maxam & Gilbert sequencing, pyrosequencing, exonuclease digestion and next-generation sequencing methods).

In some embodiments, the amplification includes a labeled primer or probe, thereby allowing detection of the amplification products corresponding to that primer or probe. In particular embodiments, the amplification can include a multiplicity of labeled primers or probes; such primers can be distinguishably labeled, allowing the simultaneous detection of multiple amplification products.

In some embodiments, the amplification products are detected by any of a number of methods such as gel electrophoresis, column chromatography, hybridization with a nucleic acid probe, or sequencing the amplicon.

Detectable labels can be used to identify the primer or probe hybridized to a genomic nucleic acid or amplicon. Detectable labels include but are not limited to fluorophores, isotopes (e.g., $^{32}P$, $^{33}P$, $^{35}S$, $^{3}H$, $^{14}C$, $^{125}I$, $^{131}I$) electron-dense reagents (e.g., gold, silver), nano articles enzymes commonly used in an ELISA (e.g., horseradish peroxidase, beta-galactosidase, luciferase, alkaline phosphatase), chemiluminiscent compounds, colorimetric labels (e.g., colloidal gold), magnetic labels (e.g., Dynabeads®), biotin, digoxigenin, haptens, proteins for which antisera or monoclonal antibodies are available, ligands, hormones, oligonucleotides capable of forming a complex with the corresponding oligonucleotide complement.

In one embodiment, a primer or probe is labeled with a fluorophore that emits a detectable signal. The term "fluorophore" as used herein refers to a molecule that absorbs light at a particular wavelength (excitation frequency) and subsequently emits light of a longer wavelength (emission frequency). While a suitable reporter dye is a fluorescent dye, any reporter dye that can be attached to a detection reagent such as an oligonucleotide probe or primer is suitable for use in the methods described. Suitable fluorescent moieties include, but are not limited to, the following fluorophores working individually or in combination: 4-acetamido-4'-isothiocyanatostilbene-2,2'disulfonic acid; acridine and derivatives, e.g., acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET); fluorescamine; IR144; IR1446; lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; and tetramethyl rhodamine isothiocyanate (TRITC).

In some aspects, the primer or probe is further labeled with a quencher dye such as Tamra, Dabcyl, or Black Hole Quencher®(BHQ), especially when the reagent is used as a self-quenching probe such as a TaqMan®(U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, *PCR Method Appl.*, 4:357-362; Tyagi et al, 1996, *Nature Biotechnology*, 14:303-308; Nazarenko et al., 1997, *Nucl. Acids Res.*, 25:2516-2521; U.S. Pat. Nos. 5,866,336 and 6,117,635).

In some aspects, methods for real time PCR use fluorescent primers/probes, such as the TaqMan® primers/probes (Heid, et al., *Genome Res* 6: 986-994, 1996), molecular beacons, and Scorpion™ primers/probes. Real-time PCR quantifies the initial amount of the template with more specificity, sensitivity and reproducibility, than other forms of quantitative PCR, which detect the amount of final amplified product. Real-time PCR does not detect the size of the amplicon. The probes employed in Scorpion®™ and TaqMan® technologies are based on the principle of fluorescence quenching and involve a donor fluorophore and a quenching moiety. The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety. The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Forster or fluorescence resonance energy transfer ("FRET"). Quenching by FRET is generally used in TaqMan® primers/probes while proximal quenching is used in molecular beacon and Scorpion™ type primers/probes.

The detectable label can be incorporated into, associated with or conjugated to a nucleic acid primer or probe. Labels can be attached by spacer arms of various lengths to reduce potential steric hindrance or impact on other useful or desired properties. See, e.g., Mansfield, *Mol. Cell. Probes* (1995), 9:145-156.

Detectable labels can be incorporated into nucleic acid probes by covalent or non-covalent means, e.g., by transcription, such as by random-primer labeling using Klenow polymerase, or nick translation, or, amplification, or equivalent as is known in the art. For example, a nucleotide base is conjugated to a detectable moiety, such as a fluorescent dye, e.g., Cy3™ or Cy5™ and then incorporated into nucleic acid probes during nucleic acid synthesis or amplification. Nucleic acid probes can thereby be labeled when synthesized using Cy3™- or Cy5™-dCTP conjugates mixed with unlabeled dCTP.

Nucleic acid probes can be labeled by using PCR or nick translation in the presence of labeled precursor nucleotides, for example, modified nucleotides synthesized by coupling allylamine-dUTP to the succinimidyl-ester derivatives of the fluorescent dyes or haptens (such as biotin or digoxigenin) can be used; this method allows custom preparation of most common fluorescent nucleotides, see, e.g., Henegariu et al., *Nat. Biotechnol.* (2000), 18:345-348.

Nucleic acid probes can be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology can also be used to label proteins by binding to nitrogen and sulfur containing side chains of amino acids. See, e.g., U.S. Pat. Nos. 5,580,990; 5,714,327; and 5,985, 566; and European Patent No. 0539466.

Labeling with a detectable label also can include a nucleic acid attached to another biological molecule, such as a nucleic acid, e.g., an oligonucleotide, or a nucleic acid in the form of a stem-loop structure as a "molecular beacon" or an "aptamer beacon". Molecular beacons as detectable moieties are described; for example, Sokol (*Proc. Natl. Acad. Sci. USA* (1998), 95:11538-11543) synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (Biochemistry (2001), 40:9387-9395), describing a molecular beacon consist of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi, Anal. Biochem. (2001), 294:126-131; Poddar, *Mol. Cell. Probes* (2001), 15:161-167; Kaboev, *Nucleic Acids Res*. (2000), 28:E94. Aptamer beacons can adopt two or more conformations, one of which allows ligand binding. A fluorescence-quenching pair is used to report changes in conformation induced by ligand binding. See also, e.g., Yamamoto et al., *Genes Cells* (2000), 5:389-396; Smimov et al., *Biochemistry* (2000), 39:1462-1468.

The nucleic acid primer or probe can be indirectly detectably labeled via a peptide. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). A label can also be attached via a second peptide that interacts with the first peptide (e.g., S-S association).

As readily recognized by one of skill in the art, detection of the complex containing the nucleic acid from a sample hybridized to a labeled probe can be achieved through use of a labeled antibody against the label of the probe. In one example, the probe is labeled with digoxigenin and is detected with a fluorescent labeled anti-digoxigenin antibody. In another example, the probe is labeled with FITC, and detected with fluorescent labeled anti-FITC antibody. These antibodies are readily available commercially. In another example, the probe is labeled with FITC, and detected with anti-FITC antibody primary antibody and a labeled anti-anti FITC secondary antibody.

Nucleic acids can be amplified prior to detection or can be detected directly during an amplification step (i.e., "real-time" methods, such as in TaqMan® and Scorpion™ methods). In some embodiments, the target sequence is amplified using a labeled primer such that the resulting amplicon is detectably labeled. In some embodiments, the primer is fluorescently labeled. In some embodiments, the target sequence is amplified and the resulting amplicon is detected by electrophoresis.

With regard to the exemplary primers and probes, those skilled in the art will readily recognize that nucleic acid molecules can be double-stranded molecules and that reference to a particular site on one strand refers, as well, to the corresponding site on a complementary strand. In defining a variant position, allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference can be made to either strand in order to refer to a particular variant position, allele, or nucleotide sequence. Probes and primers, can be designed to hybridize to either strand and detection methods disclosed herein can generally target either strand.

In some embodiments, the primers and probes comprise additional nucleotides corresponding to sequences of universal primers (e.g., T7, M13, SP6, T3) which add the additional sequence to the amplicon during amplification to permit further amplification and/or prime the amplicon for sequencing.

Methods of Treatment

The disclosure further provides methods of treating a patient selected by any method of the above embodiments, or identified as likely to experience a more favorable clinical outcome by any of the above methods, following the therapy. In some embodiments, the methods entail administering to the patients such a therapy.

In some embodiments, provided are methods for treating a cancer patient selected for treatment based on the presence of the genotype of (G/G) for the rs2280789, or (G/G) for the rs3817655 in a biological sample from the patient, comprising administering to the patient a therapy comprising an effective amount of regorafenib or an equivalent thereof. In some embodiments, provided are methods for treating a cancer patient selected for treatment based on the presence of the genotype of (G/G) for the rs2280789, or (G/G) for the rs3817655 in a biological sample from the patient, comprising, or alternatively consisting essentially of, or yet further consisting of, administering to the patient a therapy comprising a therapeutically effective amount of regorafenib or an equivalent thereof.

In some embodiments, provided are methods for treating a cancer patient selected for treatment based on the presence of the genotype of (A/G) or (G/G) for the rs7527092 polymorphism, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 in a biological sample from the patient, comprising administering to the patient a therapy comprising an effective amount of regorafenib or an equivalent thereof. In some embodiments, the patient is treated with a regorafenib-free and/or regorafenib-equivalent-free therapy if the genotype of (A/G) or (G/G) for the rs7527092 polymorphism, or (G/A) or (A/A) for the rs2071559, or (G/G) for the rs2071559 and (A/G) or (G/G) for the rs6563 and (A/G) or (G/G) for the rs2442599, or (A/A) for the rs7527092 and (T/C) or (T/T) for the rs2268614, or (A/G) or (A/A) for the rs2071559 and (C/C) for the rs3125001 and (A/G) or (A/A) for the rs2916702 is not present in the sample. In some embodiments, the patient is treated with a regorafenib-free and/or regorafenib-equivalent-free therapy if the genotype of (A/A) for the rs7527092 polymorphism, or (G/G) for the rs2071559, or (G/G) for the rs2071559 and (A/A) for the rs6563 and (A/A) for the rs2442599, or (A/A) for the rs7527092 and (C/C) for the rs2268614, or (G/G) for the rs2071559 and (T/C) or (T/T) for the rs3125001 and (G/G) for the rs2916702 is present in the sample.

In some aspects, the patient is selected by a method comprising screening a tissue or cell sample isolated from the patient for the rs2280789, rs3817655, rs7527092 and/or rs2071559 and/or the combination of rs2071559 and rs6563 and rs2442599, and/or the combination of rs7527092 and rs2268614, and/or the combination of rs2071559 and rs3125001 and rs2916702 polymorphism. Exemplary methods for screening are described in the diagnostic methods provided above and throughout the present disclosure. Any such diagnostic methods disclosed for the detection of the rs2280789, rs3817655, rs7527092 and/or rs2071559, and/or the combination of rs2071559 and rs6563 and rs2442599, and/or the combination of rs7527092 and rs2268614, and/or the combination of rs2071559 and rs3125001 and rs2916702 polymorphism can be combined with the treatment methods provided herein.

In some aspects, the patient suffers from colorectal cancer. In some aspects, the patient suffers from gastrointestinal stromal cancer. In some aspects, the patient suffers from non-metastatic cancer or metastatic cancer. In some aspects, the colorectal cancer is colon cancer. In some aspects, the colorectal cancer is rectal cancer.

Exemplary dosing schedules for the treatment of cancer with regorafenib or an equivalent thereof include but are not limited to a dose of 160 mg regorafenib or an equivalent thereof taken orally once daily for the first 21 days of each 28 day cycle, and continue until disease progression or unacceptable toxicity.

The methods are useful in the assistance of an animal, a mammal or yet further a human patient. For the purpose of illustration only, a mammal includes but is not limited to a human, a simian, a murine, a bovine, an equine, a porcine or an ovine subject. Accordingly, a formulation comprising the necessary therapy or equivalent thereof is further provided herein. The formulation can further comprise one or more preservatives or stabilizers.

The agents or drugs can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates.

Various delivery systems are known and can be used to administer a chemotherapeutic agent of the disclosure, e.g., encapsulation in liposomes, microparticles, microcapsules, expression by recombinant cells, receptor-mediated endocytosis. See e.g., Wu and Wu (1987) J. Biol. Chem. 262: 4429-4432 for construction of a therapeutic nucleic acid as part of a retroviral or other vector, etc. Methods of delivery include but are not limited to intra-arterial, intra-muscular, intravenous, intranasal and oral routes. In a specific embodiment, it can be desirable to administer the pharmaceutical compositions of the disclosure locally to the area in need of treatment; this can be achieved by, for example, and not by way of limitation, local infusion during surgery, by injection or by means of a catheter.

The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

Also provided is a therapy or a medicament comprising an effective amount of a chemotherapeutic as described herein for treatment of a human cancer patient having the appropriate expression level of the gene of interest as identified in the experimental examples. Further provided is a therapy comprising a platinum drug, or alternatively a platinum drug therapy, for use in treating a human cancer patient having the appropriate expression level of the gene of interest as identified in the experimental examples.

Methods of administering pharmaceutical compositions are well known to those of ordinary skill in the art and include, but are not limited to, oral, microinjection, intravenous or parenteral administration. The compositions are intended for topical, oral, or local administration as well as intravenously, subcutaneously, or intramuscularly. Administration can be effected continuously or intermittently throughout the course of the treatment. Methods of determining the most effective means and dosage of administration are well known to those of skill in the art and will vary with the cancer being treated and the patient and the subject being treated. Single or multiple administrations can be carried out with the dose level and pattern being selected by the treating physician.

Kits

Kits or panel for use in detecting the rs2280789, rs3817655, rs7527092 and/or rs2071559, and/or the combination of rs2071559 and rs6563 and rs2442599, and/or the combination of rs7527092 and rs2268614, and/or the combination of rs2071559 and rs3125001 and rs2916702 polymorphisms in patient biological samples are provided. In some embodiments, a kit comprises at least one reagent necessary to perform the assay. For example, the kit can comprise an enzyme, a buffer or any other necessary reagent (e.g. PCR reagents and buffers). For example, in some aspects, a kit contains, in an amount sufficient for at least one assay, any of the hybridization assay probes, amplification primers, and/or antibodies suitable for detection in a packaging material. In some embodiments, the kit or panel comprises primer and/or probes suitable for screening for the rs2280789, rs3817655, rs7527092, rs2071559, rs2268614, rs6563, rs2442599, rs3125001, rs2916702 polymorphisms.

The various components of the kit can be provided in a variety of forms. For example, in some aspects, the required enzymes, the nucleotide triphosphates, the probes, primers, and/or antibodies are be provided as a lyophilized reagent. These lyophilized reagents can be pre-mixed before lyophilization so that when reconstituted they form a complete mixture with the proper ratio of each of the components ready for use in the assay. In addition, the kits can contain a reconstitution reagent for reconstituting the lyophilized reagents of the kit. In exemplary kits for amplifying target nucleic acid derived from a cancer patients, the enzymes, nucleotide triphosphates and required cofactors for the enzymes are provided as a single lyophilized reagent that, when reconstituted, forms a proper reagent for use in the present amplification methods.

In some aspects, the kit or panel is for determining the likelihood of HFSR of a cancer patient receiving a therapy comprising regorafenib or an equivalent thereof.

In some aspects, the kit or panel is for determining the likely clinical outcome of a colorectal cancer patient receiving a therapy comprising regorafenib or an equivalent thereof. In some aspects, the kit or panel is for determining the eligibility of a cancer patient for receiving a therapy comprising regorafenib or an equivalent thereof.

Typically, the kits will also include instructions recorded in a tangible form (e.g., contained on paper or an electronic medium) for using the packaged probes, primers, and/or antibodies in a detection assay for determining the presence or amount of the rs2280789, rs3817655, rs7527092 and/or rs2071559, and/or the combination of rs2071559 and rs6563 and rs2442599, and/or the combination of rs7527092 and rs2268614, and/or the combination of rs2071559 and rs3125001 and rs2916702 polymorphism in a test sample.

In some aspects, the kits further comprise a solid support for anchoring the nucleic acid of interest on the solid support. The target nucleic acid can be anchored to the solid support directly or indirectly through a capture probe anchored to the solid support and capable of hybridizing to the nucleic acid of interest. Examples of such solid support include but are not limited to beads, microparticles (for example, gold and other nano particles), microarray, microwells, multiwell plates. The solid surfaces can comprise a first member of a binding pair and the capture probe or the target nucleic acid can comprise a second member of the binding pair. Binding of the binding pair members will anchor the capture probe or the target nucleic acid to the solid surface. Examples of such binding pairs include but are not limited to biotin/streptavidin, hormone/receptor, ligand/receptor, and antigen/antibody.

In one aspect, the kit further comprises an effective amount of the therapy. In one aspect, the therapy comprises an effective amount of regorafenib or an equivalent thereof.

The kit can comprise at least one probe or primer which is capable of specifically hybridizing to the gene of interest and instructions for use. For example, in some aspects, the kits comprise at least one of the above described nucleic acids. Exemplary kits for amplifying at least a portion of the gene of interest comprise two primers. For example, in some embodiments, the kit comprises a forward primer and a reverse primer that flank the polymorphism. For example, a forward primer comprising nucleic acid having the sequence of SEQ ID NO: 3 and a reverse primer comprising nucleic acid having the sequence of SEQ ID NO: 4, a forward primer comprising nucleic acid having the sequence of SEQ ID NO: 5 and a reverse primer comprising nucleic acid having the sequence of SEQ ID NO: 6, a forward primer comprising nucleic acid having the sequence of SEQ ID NO: 9 and a reverse primer comprising nucleic acid having the sequence of SEQ ID NO: 10, and/or a forward primer comprising nucleic acid having the sequence of SEQ ID NO: 11 and a reverse primer comprising nucleic acid having the sequence of SEQ ID NO: 12.

In some embodiments, the kit further comprises a nucleic acid probe for the detection of the amplicon. In some embodiments, the nucleic acid probe has about 5, about 10, about 15, about 20, or about 25, or about 30, about 35, about 40 or more contiguous nucleotides of any of SEQ ID NO: 1-2 or SEQ ID NO: 7-8 and overlaps the polymorphic site. In some aspects, the nucleic acid primers and/or probes are lyophilized.

In some embodiments, at least one of the primers for amplification is capable of hybridizing to the allelic variant sequence. For example, in some embodiments, at least one of the primers for amplification has about 5, about 10, about 15, about 20, or about 25, or about 30, about 35, about 40 or more contiguous nucleotides of any of SEQ ID NO: 1-2 or SEQ ID NO: 7-8 and overlaps the polymorphic site. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the surface is silica or glass. In another embodiment, the surface is a metal electrode.

The test samples used in the diagnostic kits include cells, protein or membrane extracts of cells, or biological fluids such as sputum, blood, serum, plasma, or urine. The test samples can also be a tumor cell, a normal cell adjacent to a tumor, a normal cell corresponding to the tumor tissue type, a blood cell, a peripheral blood lymphocyte, or combinations thereof. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

The kits can include all or some of the positive controls, negative controls, reagents, primers, sequencing markers, probes and antibodies described herein for determining the subject's genotype in the polymorphic region of the gene of interest or target region.

As amenable, these suggested kit components can be packaged in a manner customary for use by those of skill in the art. For example, these suggested kit components can be provided in solution or as a liquid dispersion or the like.

Typical packaging materials would include solid matrices such as glass, plastic, paper, foil, micro-particles and the like, capable of holding within fixed limits hybridization assay probes, and/or amplification primers. Thus, for example, the packaging materials can include glass vials used to contain sub-milligram (e.g., picogram or nanogram) quantities of a contemplated probe, primer, or antibodies or they can be microtiter plate wells to which probes, primers, or antibodies have been operatively affixed, i.e., linked so as to be capable of participating in an amplification and/or detection methods.

The instructions will typically indicate the reagents and/or concentrations of reagents and at least one assay method parameter which might be, for example, the relative amounts of reagents to use per amount of sample. In addition, such specifics as maintenance, time periods, temperature, and buffer conditions can also be included.

The diagnostic systems contemplate kits having any of the hybridization assay probes, amplification primers, or antibodies described herein, whether provided individually or in one of the combinations described above, for use in determining the presence or amount of rs2280789, rs3817655, rs7527092 and/or rs2071559, and/or the combination of rs2071559 and rs6563 and rs2442599, and/or the combination of rs7527092 and rs2268614, and/or the combination of rs2071559 and rs3125001 and rs2916702 polymorphism in a test sample.

The disclosure now being generally described, it will be more readily understood by reference to the following example which is included merely for purposes of illustration of certain aspects and embodiments of the present disclosure, and are not intended to limit the disclosure.

EXPERIMENTAL EXAMPLES

The first example shows that functional significant single nucleotide polymorphisms in genes involved in the degradation pathway predict likelihoods of a cancer patient experiencing HFSR from a therapy comprising an effective amount of regorafenib or an equivalent thereof.

The second example shows that functional significant single nucleotide polymorphisms in genes involved in the pathway predict clinical outcomes of cancer treated with a therapy comprising an effective amount of regorafenib or an equivalent thereof.

HFSR of grade 3-4 are among the most common grade 3-4 reverse reactions associated with a therapy with regorafenib or an equivalent thereof. In this example, single nucleotide polymorphisms (SNPs) of CCL5 were evaluated for their ability to predict the likelihood for a patient to experience HFSR from a therapy comprising an effective amount of regorafenib or an equivalent thereof.

Genomic DNA was obtained from more than 200 cancer patients receiving regorafenib and analyzed by using PCR-based direct sequencing. SNPs in CCL5 were tested to discover that the rarity (<1%) of the genotype of (G/G) for the rs2280789 polymorphism and/or the rs3817655 polymorphism (the genotype of (G/G) for the rs2280789 polymorphism and/or the rs3817655 are seen in 10% in Asian (Japanese) and 1% in Caucasian (Italian)) relates to the significant ethnic difference in severe HFSR developed by Caucasian patients compared to Japanese patients (grade 3 HFSR 16% vs 33.8% respectively, p=0.003).

Further, single nucleotide polymorphisms (SNPs) of genes involved in various angiogenic pathways were evaluated for their ability to predict clinical outcomes for cancer patient treated with a therapy comprising regorafenib or an equivalent thereof.

Still further, combinations of single nucleotide polymorphisms (SNPs) of genes involved in various angiogenic pathways were evaluated for their ability to predict clinical outcomes for cancer patient treated with a therapy comprising regorafenib or an equivalent thereof.

Genomic DNA was obtained from cancer patients in therapies comprising regorafenib or an equivalent thereof and analyzed by using PCR-based direct sequencing. Multiple functional SNPs in 11 genes (NOTCH1, IL8, CCL5, DLL4, PLGF, ANG2, TIE1, PDGFRB, VEGFR2, EGFC and VEGFA) were tested.

PCR and product sequencing were done using standard procedures. Uni- and multivariate analyses, adjusting for age, gender, rash and racial background, were carried out.

Example PCR primers used in the example are provided in the table below

Among tested patients, TIE1 rs7527092 A/A(N=41) achieved a significantly worse OS compared to G/variant carriers (N=106) in the univariate (median OS 4.7 vs 7.8 months respectively, HR=1.49 [95% CI 1.0.67], p=0.0303) and in the multivariate analysis (HR=1.72 [95% CI 1.0.58], p=0.0063).

Among tested patients, VEGFR2 rs2071559 G/G (N=39) showed a significant worse response compared to A/variant carriers (N=111) in the analysis (positive 18% vs. 41% respectively, p=0.0166), a significant worse PFS compared to A/variant carriers (N=111) in the univariate (median PFS 1.8 vs 2.3 months respectively, HR=1.49 [95% CI 1.0.67], p=0.0250) and in the multivariate analysis (HR=1.59 [95% CI 1.0.63], p=0.0197), and a significant worse OS compared to A/variant carriers (N=111) in the univariate (median OS 4.7 vs 7.0 months respectively, HR=1.45 [95% CI 1.0.69], p=0.0452).

Figure 5A:
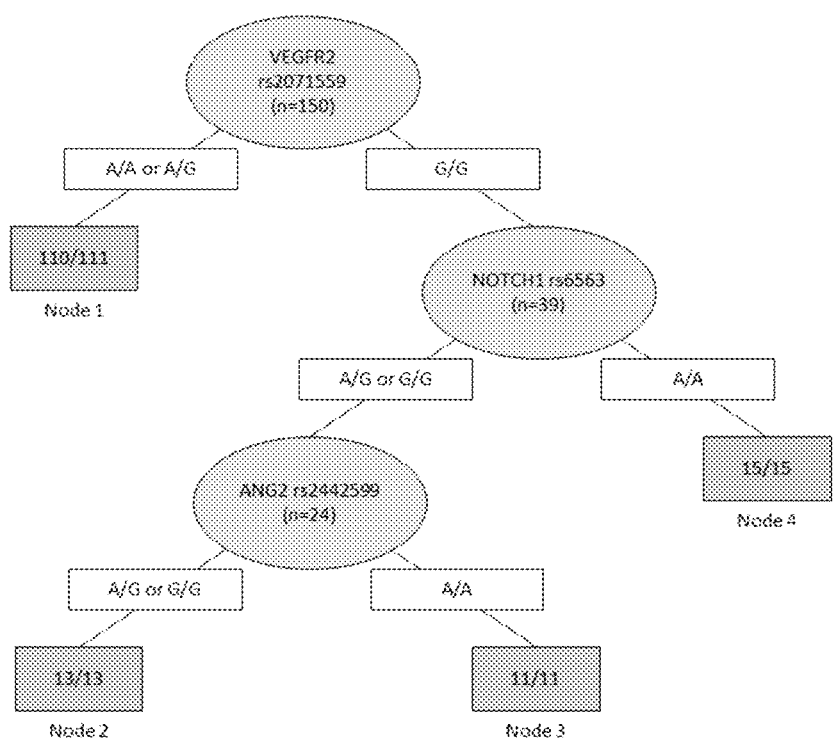
FIG. 5A illustrates recursive partitioning analysis of progression free survival of various SNPs.
Figure 5B:
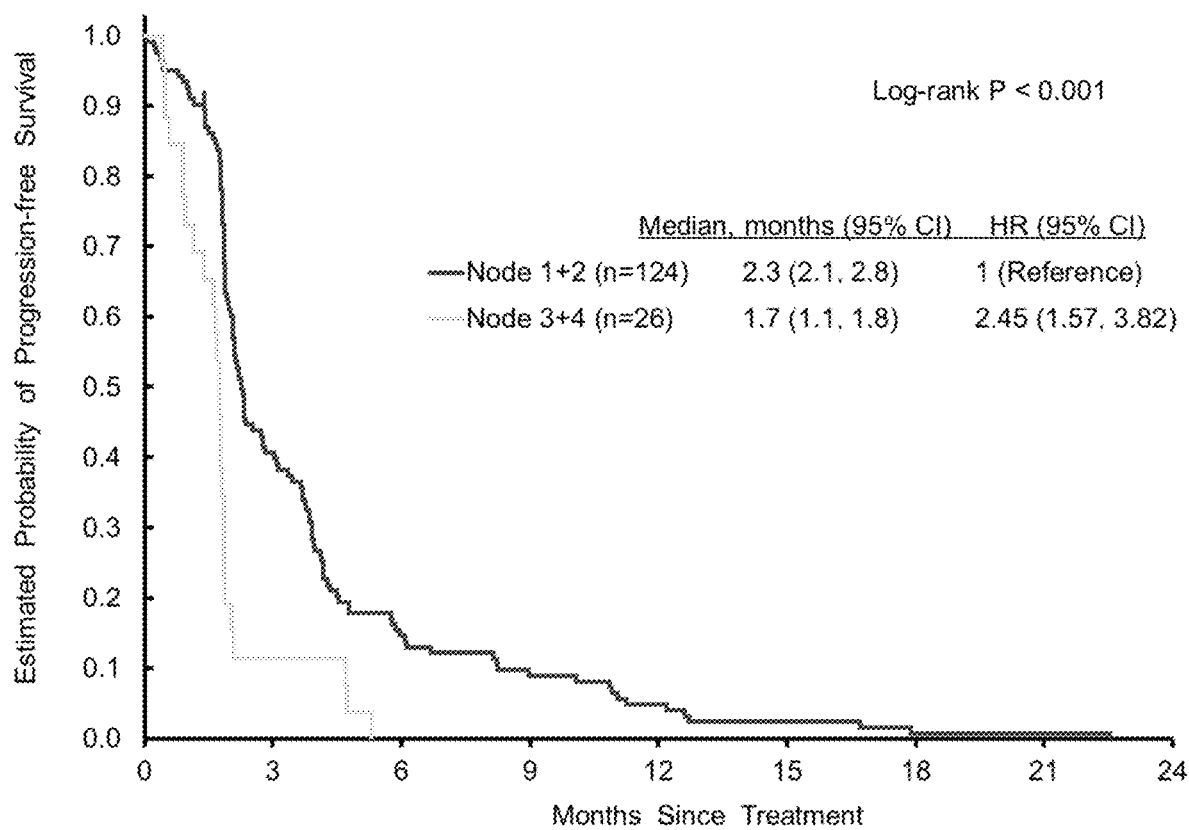
FIG. 5B illustrates progression free survival by tree model defined subgroups.

Among tested patients, NOTCH1 rs6563 A/A in combination with VEGFR2 rs2071559 G/G carriers (N=15), together with VEGFR2 rs2071559 G/G in combination of NOTCH1 rs6563 G/Variant in combination with ANG2 rs2442599 A/A carriers (N=11), showed a significant worse PFS compared to VEGFR2 rs2071559 A/variant carriers (N=111) together with VEGFR2 rs701559 G/G in combination with NOTCH1 rs6563 G/Variant in combination with ANG2 rs2442599 G/Variant carriers (N=13) in the multivariate analysis (median PFS 1.7 vs. 2.3 months respectively, HR=0.41 [95% CI 1.0 2.45], log-rank P<0.001). FIG. 5A illustrates recursive partitioning analysis of PFS. The end nodes of tree model represent subgroups of low-risk and high-risk patients based on either a single gene variant or combination of gene variants. Fractions within the end nodes indicate patients who progressed/total patients with this gene variant profile. FIG. 5B illustrates PFS by tree model defined subgroups. Combined nodes 3 and 4 defined a high-risk group based on the gene variant profile including VEGFR2 rs2071559, NOTCH1 rs6563 and ANG2 rs2442599.

Among tested patients, TIE1 rs7527092 A/A in combination with Plgf rs2268614 C/C carriers (N=9) showed a

Figure 6A:
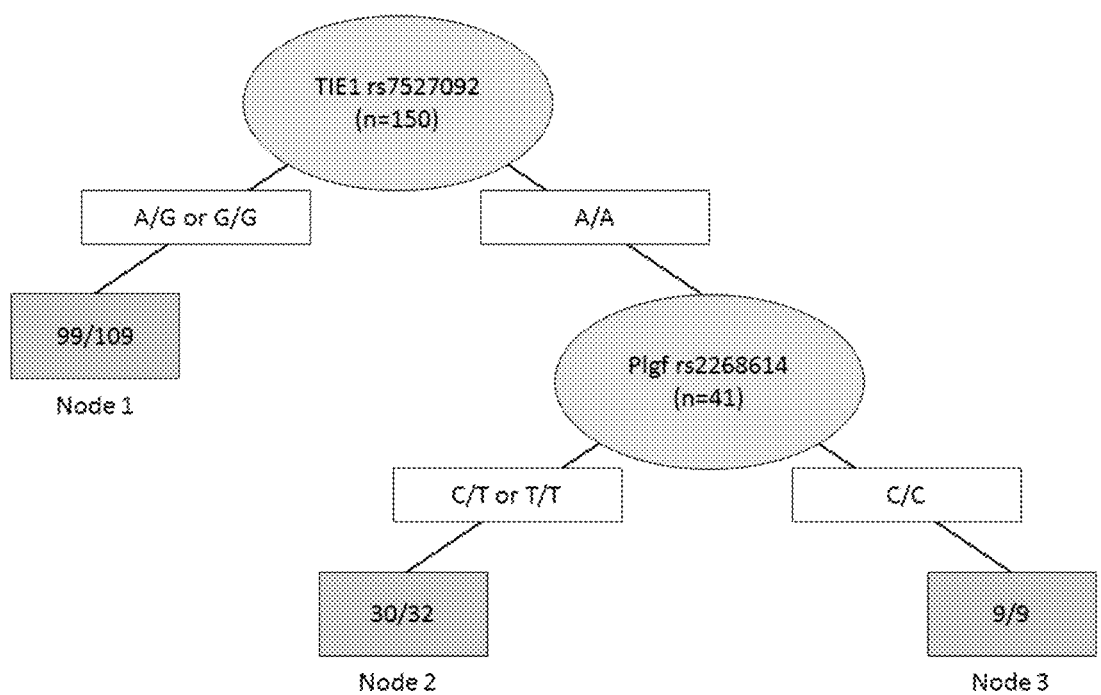
FIG. 6A illustrates recursive partitioning analysis of overall survival of various SNPs.
Figure 6B:
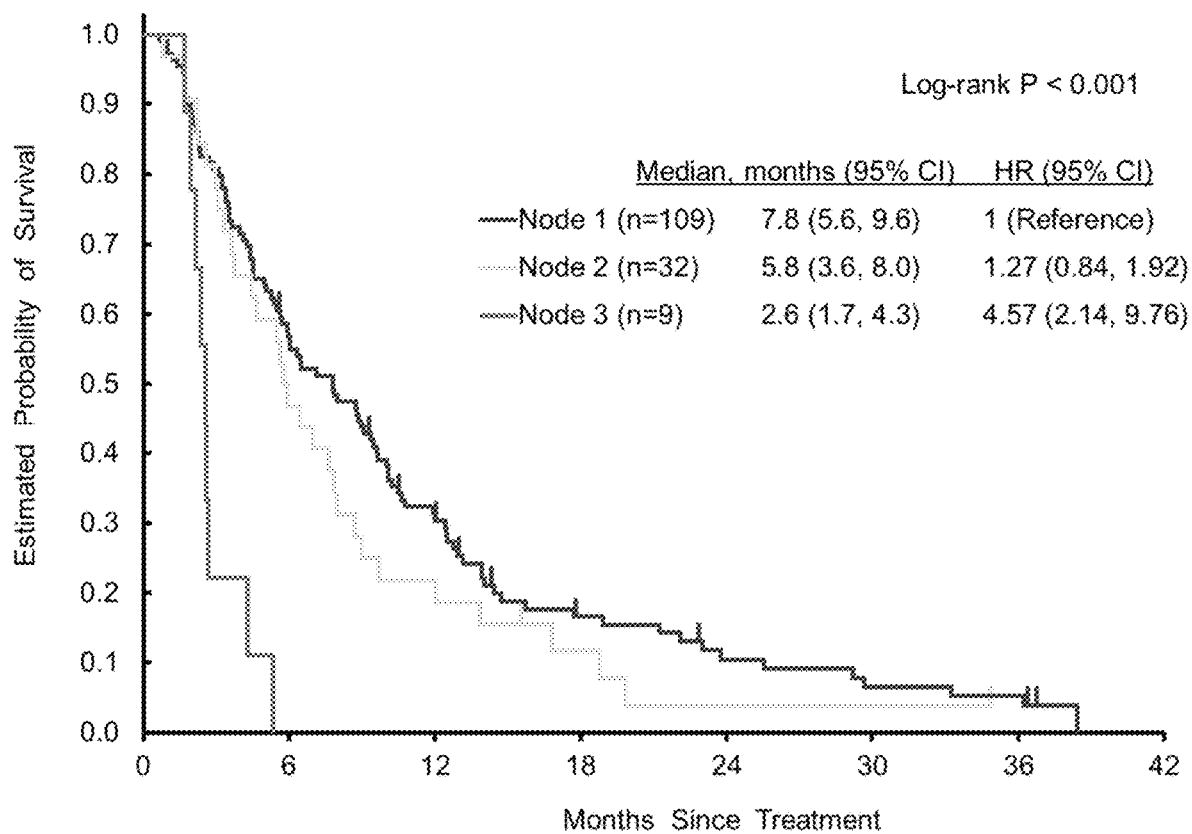
FIG. 6B illustrates overall survival by tree model defined subgroups.

| SNP | Forward primer (SEQ ID NO.) | Reverse primer (SEQ ID NO.) |
|---|---|---|
| CCL5 rs2280789 | (3) 5'ATCTCCCCAACATGAGTCCA3' | (4) 5'CCATATGTCCTGTTGTCCTTGA3' |
| CCL5 rs3817655 | (5) 5'GGGCCCAGATTCTACCACAC3' | (6) 5'GCTCATGGGGAAGGACAGTT3' |
| TIE1 rs7527092 | (9) AGGATCAATTGAGGCCAGGA | (10) TGATTAAATACATTCCTAGTGTTGTCC |
| VEGFR2 rs2071559 | (11) AGGGTATTTGTTTGGCCAGT | (12) GGCTAGGCAGGTCACTTCAA |
| NOTCH1 rs6563 | (18) GAGGCTGCCCTGAGGAGT | (19) TGTTGTGTGTCATGCCAG |
| NOTCH1 rs3125001 | (20) AGAACGCACTCGTTGATGTC | (21) GTCACGGAAGCCTACTCCTG |
| ANG2 rs2442599 | (22) CGTGGTGATTTATGGAAAGG | (23) GGGAGCATCCTGACAAAAGA |
| ANG2 rs2916702 | (24) TCCTTTTTATGTAGCTCCACTGAG | (25) AAGCAAACATCTGAGGCACA |
| Plgf rs2268614 | (26) CTGGGGTGGTAGGAGCACT | (27) GAGACGGCCAATGTCACC | significant worse OS compared to TIE1 rs7527092 G/Variant carriers (N=109), to TIE1 rs7527092 A/A in combination with Plgf rs2268614 T/Variant Carriers (N=32), respectively, in the multivariate analysis (median OS 2.6 vs. 7.8 vs. 5.8 months respectively, HR=0.22 [95% CI 1.0 4.57], HR=0.79 [95% CI 1.0 1.27], log-rank P<0.001, TIE1 rs7527092 G/Variant carriers representing the HR reference). FIG. 6A illustrates recursive partitioning analysis of OS. The end nodes of tree model represent subgroups of low-risk and high-risk patients based on either a single gene variant or combination of gene variants. Fractions within the end nodes indicate patients who deceased/total patients with this gene variant profile. FIG. 6B illustrates OS by tree model defined subgroups. Node 3 defined a high-risk group based on the gene variant profile including TIE1 rs7527092 and Plgf rs2268614.

Figure 7:
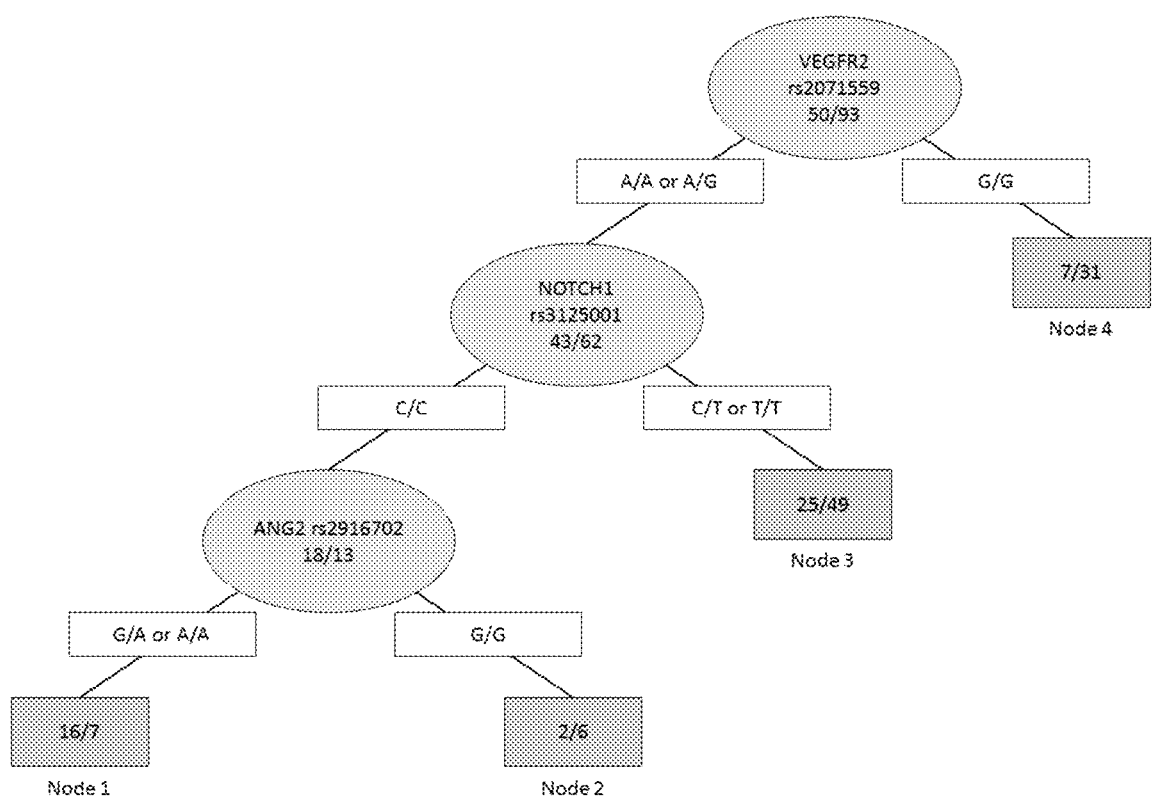
FIG. 7 illustrates recursive portioning analysis of tumor response of various SNPs.

Among tested patients, VEGFR2 rs2071559 G/G carrier (7 responsive vs. 31 non-responsive), together with VEGFR2 rs2071559 A/Variant in combination with NOTCH1 rs3125001 T/Variant carriers (25 responsive vs. 49 non-responsive), together with VEGFR2 rs2071559 A/Variant in combination with NOTCH1 rs3125001 C/C in combination with ANG2 rs2916702 G/G carriers (2 responsive vs. 6 non-responsive) showed a significant worse response to tumors compared VEGFR2 rs2071559 A/Variant in combination with NOTCH1 rs3125001 C/C in combination with ANG2 rs2916702 A/Variant carriers (16 responsive vs. 7 non-responsive) in the multivariate analysis. This study demonstrated that variations in genes may affect clinical outcome of cancer patients treated with a therapy comprising regorafenib or an equivalent thereof. FIG. 7 illustrates recursive partitioning analysis of tumor response. The end nodes of tree model represent subgroups of responder or non-responder patients based on either a single gene variant or combination of gene variants. Fractions within the end nodes indicate patients who had response/no response with this gene variant profile.

The disclosure illustratively described herein can suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosure embodied therein herein disclosed can be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for determining whether a cancer patient is likely or not likely to experience HFSR (hand foot skin reaction) from a therapy comprising administration of an effective amount of regorafenib, comprising screening a biological sample isolated from the patient for the rs2280789 polymorphism using a forward primer having the sequence of SEQ ID NO: 3 and a reverse primer having the sequence of SEQ ID NO: 4, and/or the rs3817655 polymorphism using a forward primer having the sequence of SEQ ID NO: 5 and a reverse primer having the sequence of SEQ ID NO: 6, wherein the presence of the genotype of (G/G) for the rs2280789 or (G/G) for rs3817655 indicates the patient will likely experience HFSR (hand foot skin reaction) and the absence of the (G/G) genotype indicates the patient is not likely to experience HFSR.

2. The method of claim 1, wherein screening further comprises contacting the biological sample or nucleic acid isolated from the biological sample with a labeled nucleic acid probe that specifically binds to a nucleic acid having the sequence of any of SEQ ID NO: 1-2 and overlaps the rs2280789 or rs3817655 polymorphic site.

3. The method of claim 2, wherein the nucleic acid probe comprises from 5 to 40 contiguous nucleotides of any of SEQ ID NO: 1-2, and optionally wherein the label is a fluorophore.

4. The method of claim 1, wherein screening further comprises amplifying a nucleic acid containing the rs2280789 or rs3817655 polymorphism to generate an amplicon containing the rs2280789 or rs3817655 polymorphism.

5. The method of claim 1, wherein the cancer patient is a colorectal cancer patient or a gastrointestinal stromal cancer patient.

6. The method of claim 5, wherein the patient suffers from non-metastatic cancer or metastatic cancer.

7. The method of claim 1, wherein the biological sample is one or more from the group of: a cell, a tissue sample, a tumor cell, a normal cell adjacent to a tumor, a normal cell corresponding to the tumor tissue type, a blood cell, a peripheral blood lymphocyte, blood, plasma, a fixed tissue, a frozen tissue, a biopsy tissue, a resection tissue, a microdissected tissue, or combinations thereof.

8. A method for treating a genotvped cancer patient determined to have the genotype of (G/G) for the rs2280789, or (T/T) for the rs3817655, the method comprising administering to the patient a therapy comprising a therapeutically effective amount of regorafenib.

9. The method of claim 8, wherein screening comprises contacting the biological sample or nucleic acid isolated from the biological sample with a labeled nucleic acid probe that specifically binds to a nucleic acid having the sequence of any of SEQ ID NO: 1-2 and overlaps the rs2280789 or rs3817655 polymorphic site.

10. The method of claim 9, wherein the nucleic acid probe comprises from 5 to 40 contiguous nucleotides of any of SEQ ID NO: 1-2, and optionally wherein the label is a fluorophore.

11. The method of claim 8, wherein screening comprises amplifying nucleic acid containing the rs2280789 or rs3817655 polymorphism to generate an amplicon containing the rs2280789 or rs3817655 polymorphism.

12. The method of claim 11, wherein the amplifying is performed with a forward primer having the sequence of SEQ ID NO: 3 and a reverse primer having the sequence of SEQ ID NO: 4, and/or a forward primer having the sequence of SEQ ID NO: 5 and a reverse primer having the sequence of SEQ ID NO: 6.

13. The method of claim 8, wherein the cancer patient is a colorectal cancer patient or a gastrointestinal stromal cancer patient.

14. The method of claim 8, wherein the patient suffers from non-metastatic cancer or metastatic cancer.

15. The method of claim 8, wherein the biological sample is one or more from the group of: a cell, a tissue sample, a tumor cell, a normal cell adjacent to a tumor, a normal cell corresponding to the tumor tissue type, a blood cell, a peripheral blood lymphocyte, blood, plasma, a fixed tissue, a frozen tissue, a biopsy tissue, a resection tissue, a microdissected tissue, or combinations thereof.

* * * * *